US006908921B2

(12) United States Patent
Su et al.

(10) Patent No.: US 6,908,921 B2
(45) Date of Patent: Jun. 21, 2005

(54) QUINOXALINONE DERIVATIVES AS BRADYKININ B1 ANTAGONISTS

(75) Inventors: Dai-Shi Su, Dresher, PA (US); Mark G. Bock, Hatfield, PA (US)

(73) Assignee: Merck & Co., Inc., Rahway, NJ (US)

( * ) Notice: Subject to any disclaimer, the term of this patent is extended or adjusted under 35 U.S.C. 154(b) by 160 days.

(21) Appl. No.: 10/614,539

(22) Filed: Jul. 7, 2003

(65) Prior Publication Data

US 2004/0132733 A1 Jul. 8, 2004

Related U.S. Application Data

(60) Provisional application No. 60/433,146, filed on Dec. 13, 2002.

(51) Int. Cl.$^7$ .......................... A01N 43/58; A01N 43/60; A61K 31/495; A61K 31/50; C07D 241/36

(52) U.S. Cl. ........................................ 514/249; 544/354

(58) Field of Search .......................... 514/249; 544/354

(56) References Cited

U.S. PATENT DOCUMENTS 6,369,057 B1    4/2002   Billhardt et al.

FOREIGN PATENT DOCUMENTS

| DE | 43 41 663 A1 | 7/1993 |
|---|---|---|
| JP | 05331151 | * 12/1993 |
| WO | WO 03/007958 A1 | 1/2003 |
| WO | WO 03/093245 A1 | 11/2003 |

OTHER PUBLICATIONS

Dai–Shi Su, et al., *J. Am. Chem. Soc.*, 125, pp 7516–7517 (2003).
V. D. Romanenko, et al., (English version—translated from): *Khimiya Geterotsiklicheskikh Soedinenii*, 2, pp 264–266 (1973).
American Chemical Society CAS Registry No. 484642–50–4, and associated citations in the CHEMCATS Database of STN Online, 2003.
American Chemical Society CAS Registry No. 484641–37–4, and associated citations in the CHEMCATS Database of STN Online, 2003.
American Chemical Society CAS Registry No. 484049–33–4, and associated citations in the CHEMCATS Database of STN Online, 2003.
American Chemical Society CAS Registry No. 484049–31–2, and associated citations in the CHEMCATS Database of STN Online, 2003.
American Chemical Society CAS Registry No. 484049–30–1, and associated citations in the CHEMCATS Database of STN Online, 2003.
American Chemical Society CAS Registry No. 476410–20–5, and associated citations in the CHEMCATS Database of STN Online, 2003.
American Chemical Society CAS Registry No. 476410–19–2, and associated citations in the CHEMCATS Database of STN Online, 2003.
American Chemical Society CAS Registry No. 476410–18–1, and associated citations in the CHEMCATS Database of STN Online, 2003.
American Chemical Society CAS Registry No. 476410–17–0, and associated citations in the CHEMCATS Database of STN Online, 2003.
American Chemical Society CAS Registry No. 476409–78–6, and associated citations in the CHEMCATS Database of STN Online, 2003.
American Chemical Society CAS Registry No. 476409–77–5, and associated citations in the CHEMCATS Database of STN Online, 2003.
American Chemical Society CAS Registry No. 476409–76–4, and associated citations in the CHEMCATS Database of STN Online, 2003.
American Chemical Society CAS Registry No. 476409–75–3, and associated citations in the CHEMCATS Database of STN Online, 2003.
American Chemical Society CAS Registry No. 476409–74–2, and associated citations in the CHEMCATS Database of STN Online, 2003.
American Chemical Society CAS Registry No. 476409–70–8, and associated citations in the CHEMCATS Database of STN Online, 2003.
American Chemical Society CAS Registry No. 476409–69–5, and associated citations in the CHEMCATS Database of STN Online, 2003.
American Chemical Society CAS Registry No. 476409–68–4, and associated citations in the CHEMCATS Database of STN Online, 2003.
American Chemical Society CAS Registry No. 476409–67–3, and associated citations in the CHEMCATS Database of STN Online, 2003.
American Chemical Society CAS Registry No. 476409–65–1, and associated citations in the CHEMCATS Database of STN Online, 2003.
American Chemical Society CAS Registry No. 471917–04–1, and associated citations in the CHEMCATS Database of STN Online, 2003.
American Chemical Society CAS Registry No. 353745–13–8, and associated citations in the CHEMCATS Database of STN Online, 2003.
American Chemical Society CAS Registry No. 333408–60–9, and associated citations in the CHEMCATS Database of STN Online, 2003.

(Continued)

*Primary Examiner*—James O. Wilson
*Assistant Examiner*—Zachary C. Tucker
(74) *Attorney, Agent, or Firm*—Mollie M. Yang; David L. Rose

(57) ABSTRACT

2-Quinoxalinone derivatives are bradykinin B1 antagonists or inverse agonists useful in the treatment or prevention of symptoms such as pain and inflammation associated with the bradykinin B1 pathway.

19 Claims, No Drawings

OTHER PUBLICATIONS

American Chemical Society CAS Registry No. 309923–99–7, and associated citations in the CHEMCATS Database of STN Online, 2003.

Dai–Shi Su, et al., Discovery of a potent, non–peptide bradykinin B1 receptor antagonist, 226th ACS National Meeting (New York City, Sep. 10, 2003).

* cited by examiner

QUINOXALINONE DERIVATIVES AS BRADYKININ B1 ANTAGONISTS

CROSS REFERENCE TO RELATED APPLICATIONS

This application claims the benefit of U.S. Provisional Application No. 60/433,146, filed Dec. 13, 2002.

BACKGROUND OF THE INVENTION

This invention is directed to quinoxalinone compounds. In particular, this invention is directed to quinoxalinone compounds that are bradykinin antagonists or inverse agonists.

Bradykinin ("BK") is a kinin which plays an important role in the pathophysiological processes accompanying acute and chronic pain and inflammation. Bradykinin (BK), like other kinins, is an autacoid peptide produced by the catalytic action of kallikrein enzymes on plasma and tissue precursors termed kininogens. The biological actions of BK are mediated by at least two major G-protein-coupled BK receptors termed B1 and B2. It is generally believed that B2 receptors, but not B1 receptors, are expressed in normal tissues and that inflammation, tissue damage or bacterial infection can rapidly induce B1 receptor expression. This makes the B1 receptor a particularly attractive drug target. The putative role of kinins, and specifically BK, in the management of pain and inflammation has provided the impetus for developing potent and selective BK antagonists. In recent years, this effort has been heightened with the expectation that useful therapeutic agents with analgesic and anti-inflammatory properties would provide relief from maladies mediated through a BK receptor pathway (see e.g., M. G. Bock and J. Longmore, Current Opinion in Chem. Biol., 4:401–406(2000)). Accordingly, there is a need for novel compounds that are effective in blocking or reversing activation of bradykinin receptors. Such compounds would be useful in the management of pain and inflammation, as well as in the treatment or prevention of diseases and disorders mediated by bradykinin; further, such compounds are also useful as research tools (in vivo and in vitro).

U.S. Pat. No. 6,369,057 discloses antiviral quinoxalines of the formula:

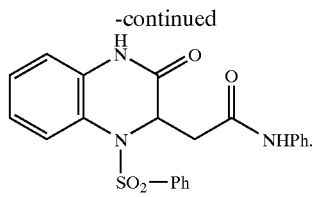

Romanenko et al, Khim. Geterotsikl. Soedin., 1973, No. 2, p. 264–6, reports compounds of the formulae:

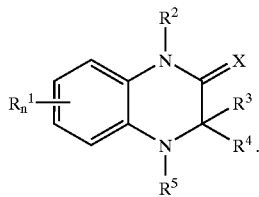

and

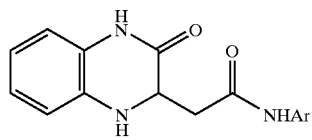

No biological activity is reported for these compounds.

SUMMARY OF THE INVENTION

The present invention provides novel quinoxaline derivatives which are bradykinin antagonists or inverse agonists, pharmaceutical compositions containing such compounds, and methods of using them as therapeutic agents.

DETAILED DESCRIPTION OF THE INVENTION

The present invention provides compounds of formula I

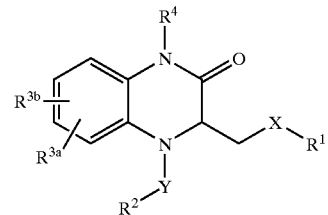

and pharmaceutically acceptable salts thereof,
wherein
X is selected firm
   (1) —$(CH_2)_m C(O)NR^b$—,
   (2) —$(CH_2)_m NR^b C(O)$—,
   (3) —$(CH_2)_m C(O)O$—,
   (4) —$(CH_2)_m S(O)_m$—,
   (5) —$(CH_2)_m O$—,
   (6) —$(CH_2)_m NR^b$—,
   (7) —C(O)—,
   (8) HC=CH, and
   (9) —$(CH_2)_m$—;
Y is selected from
   (1) —C(O)—,
   (2) —C(O)O—,
   (3) —$SO_2$— and,
   (4) —$CH_2$—;
$R^1$ is $(CH_2)_n$-phenyl substituted with a group selected from 1-imidazolyl, 2-imidazolyl, 4,5-dihydro-2-imidazolyl, and 1,2,4-triazol-4-yl; wherein the imidazolyl, dihydroimidazolyl, and triazolyl rings are each optionally substituted with 1 or 2 $C_{1-4}$alkyl groups;
$R^2$ is selected from:
   (1) $C_{1-6}$ alkyl optionally substituted with 1 to 3 halogen atoms,
   (2) $C_{3-7}$ cycloalkyl,
   (3) aryl,
   (4) ara-$C_{1-4}$alkyl,
wherein aryl and aralkyl are optionally substituted with 1 to 4 groups independently selected from halogen, $C_{1-4}$ alkyl optionally substituted with 1 to 5 halogen atoms, hydroxy, $C_{1-4}$ alkoxy optionally substituted with 1 to 5 halogen atoms, nitro, cyano and NR$^b$R$^c$; and wherein aryl is selected from phenyl, naphthyl, pyridyl, isoquinolinyl, and thienyl;
R$^{3a}$ and R$^{3b}$ are independently selected from
  (1) H,
  (2) halogen,
  (3) C$_{1-6}$ alkyl,
  (4) hydroxy,
  (5) cyano,
  (6) nitro,
  (7) C$_{1-6}$ alkoxy, and
  (8) trifluoromethyl;
R$^4$ is selected from
  (1) H,
  (2) C$_{1-4}$ alkyl, optionally substituted with 1-5 halogen atoms,
  (3) C$_{3-7}$ cycloalkyl,
  (4) (CH$_2$)$_p$CO$_2$R$^d$, and
  (5) (CH$_2$)$_p$CONR$^b$R$^c$;
R$^b$ and R$^c$ are independently selected from
  (1) H, and
  (2) C$_{1-6}$ alkyl, or
R$^b$ and R$^c$ together complete a 4- to 7-membered ring optionally containing a ring O or N—R$^d$ group;
R$^d$ is H or C$_{1-4}$ alkyl,
m is 0, 1 or 2;
n is 0 to 10; and
p is 1 or 2.

In one subset of formula I are compounds of formula Ia:

wherein Y is —SO$_2$—, —CO— or CH$_2$; R$^2$ is optionally substituted phenyl or naphthyl; R$^{3a}$ is hydrogen or a halogen; R$^4$ is hydrogen or C$_{1-4}$alkyl; and R$^1$ is —(CH$_2$)$_{n'}$-(4-substituted phenyl) wherein n' is 0 to 5 and the substituent is selected from 4,5-dihydro-2-imidazolyl optionally substituted with a C$_{1-4}$alkyl group, 2-imidazolyl, 1-imidazolyl, and 1,2,4-tiazol-4-yl.

In one embodiment of formula Ia are compounds wherein R$^2$ is 3,4-dichlorophenyl, 2-naphthyl or 2,4,6-trimethylphenyl.

In a second embodiment of formula Ia are compounds wherein R$^1$ is —(CH$_2$)$_{0-2}$-(4-substituted phenyl) wherein the substituent is selected from 4,5-dihydro-2-imidazolyl optionally substituted with a C$_{1-4}$alkyl group, 2-imidazolyl, 1-imidazolyl and 1,2,4-triazol-4-yl.

In a fourth embodiment of formula Ia are compounds wherein the stereoconfiguration at position 3 of the 2-quinoxalinone ring is R.

In another subset of formula I are compounds wherein the stereoconfiguration at position 3 of the 2-quinoxalinone ring is R.

In a third subset of formula I are compounds where X is selected from C(O)O, CH$_2$, CH$_2$SO$_2$, NHC(O) and CH$_2$NHC(O); Y is —SO$_2$—, —CO— or CH$_2$; R$^2$ is optionally substituted phenyl or naphthyl; R$^{3a}$ is hydrogen or a halogen; R$^4$ is hydrogen or C$_{1-4}$alkyl; and R$^1$ is —(CH$_2$)$_{n'}$-(4-substituted phenyl) wherein n' is 0 to 5 and the substituent is selected from 4,5-dihydro-2-imidazolyl optionally substituted with a C$_{1-4}$alkyl group, 2-imidazolyl, 1-imidazolyl and 1,2,4-triazol-4-yl.

In a fourth set of formula I are compounds of formula Ib:

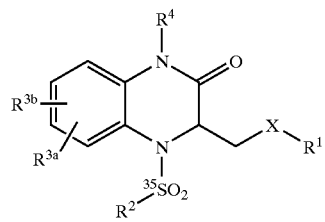

wherein all the variables are as defined under formula I.

Unless otherwise stated, the following terms have the meanings indicated below:

"Alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like.

"Alkenyl" means a linear or branched carbon chain containing at least one C=C bond. Examples of alkenyl include allyl, 2-butenyl, 3-butenyl, 1-methyl-2-propenyl, and the like.

"Aryl" means a 6–14 membered carbocyclic aromatic ring system comprising 1–3 benzene rings. If two or more aromatic rings are present, then the rings are fused. Examples include phenyl and naphthyl.

"Cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydro-naphthalene, adamantane, indanyl, indenyl, fluorenyl, 1,2,3,4-tetrahydronaphthalene and the like.

"Halogen" means fluorine, chlorine, bromine and iodine.

"Optionally substituted" is intended to include both substituted and unsubstituted. Thus, for example, optionally substituted aryl could re nt a pentafluorophenyl or a phenyl ring.

Optical Isomers-Diastereomers-Geometric Isomers-Tautomers

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of formula I encompass those labeled with a radioisotope such as $^{35}S$. Radiolabeled compounds are utilized in biological assays as described herein.

Salts

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

Prodrugs

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active indent is being administered. The pharmaceutical compositions may be conveniently presented in unit dosage form and prepared by any of the methods well known in the art of pharmacy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid It is preferable that the mixture forms unit dose suppositories. Suitable carriers include cocoa butter and other materials commonly used in the art The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

Utilities

Compounds of this invention are antagonists or inverse agonists of bradykinin receptor, in particular the bradykinin B1 receptor, and as such are useful in the treatment and prevention of diseases and conditions mediated through the bradykinin receptor pathway such as pain and inflammation. The compounds would be effective in the treatment or prevention of pain including, for example, visceral pain (such as pancreatitis, interstitial cystitis, renal colic), neuropathic pain (such as postherpetic neuralgia, nerve injury, the "dynias", e.g., vulvodynia, phantom limb pain, root avulsions, painful traumatic mononeuropathy, painful polyneuropathy), central pain syndromes (potentially caused by virtually any lesion at any level of the nervous system), and postsurgical pain syndromes (eg, postmastectomy syndrome, postthoracotomy syndrome, stump pain)), bone and joint pain (osteoarthritis), repetitive motion pain, dental pain, cancer pain, myofascial pain (muscular injury, fibromyalgia), perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout).

Further, the compounds of this invention can also be used to treat hyperreactive airways and to teat inflammatory events associated with airways disease e.g. asthma including allergic asthma (atopic or non-atopic) as well as exercise-induced bronchoconstriction, occupational asthma, viral- or bacterial exacerbation of asthma, other non-allergic asthmas and "wheezy-infant syndrome". Compounds of the present invention may also be used to treat chronic obstructive pulmonary disease including emphysema, adult respiratory distress syndrome, bronchitis, pneumonia, allergic rhinitis (seasonal and perennial), and vasomotor rhinitis. They may also be effective against pneumoconiosis, including aluminosis, anthracosis, asbestosis, chalicosis, ptilosis, siderosis, silicosis, tabacosis and byssinosis.

Compounds of the present invention may also be used for the treatment of inflammatory bowel disease including Crohn's disease and ulcerative colitis, irritable bowel syndrome, pancreatitis, nephritis, cystitis (interstitial cystitis), uveitis, inflammatory skin disorders such as psoriasis and eczema, rheumatoid arthritis and edema resulting from trauma associated with burns, sprains or fracture, cerebral edema and angioedema. They may be used to treat diabetic vasculopathy, diabetic neuropathy, diabetic retinopathy, post capillary resistance or diabetic symptoms associated with insulitis (e.g. hyperglycemia, diuresis, proteinuria and increased nitrite and kallikrein urinary excretion). They may be used as smooth muscle relaxants for the treatment of spasm of the gastrointestinal tract or uterus. Additionally, they may be effective against liver disease, multiple sclerosis, cardiovascular disease, e.g. atherosclerosis, congestive heart failure, myocardial infarct; neurodegenerative diseases, eg. Parkinson's and Alzheimers disease, epilepsy, septic shock e.g. as anti-hypovolemic and/or anti-hypotensive agents, headache including cluster headache, migraine including prophylactic and acute use, closed head trauma, cancer, sepsis, gingivitis, osteoporosis, benign prostatic hyperplasia and hyperactive bladder. Animal models of these diseases and conditions are generally well known in the art, and may be suitable for evaluating compounds of the present invention for their potential utilities.

Compounds of the present invention are also useful as research tools (in vivo, in vitro and ex vivo). In one aspect a compound of the present invention is labeled with a radionuclide, preferably $^{35}S$, and used in a brain receptor occupancy assay to assess the ability of test compounds to penetrate the blood brain barrier as well as the ability to distribute into the tissue and bind to the receptor. One such receptor occupancy assay using transgenic animal expressing human bradykinin B1 receptor is described hereinbelow.

Dosage and Administration

The compounds of this invention are useful in the treatment of pain and inflammation by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

The compounds would be effective in the treatment or prevention of pain including, for example, bone and joint pain (osteoarthritis), repetitive motion pain, dental pain, cancer pain, myofascial pain (muscular injury, fibromyalgia), perioperative pain (general surgery, gynecological) and chronic pain by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

In particular, inflammatory pain such as, for example, inflammatory airways disease (chronic obstructive pulmonary disease) would be effectively treated by the compounds of this invention by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Further, the compounds of this invention can additionally be used to treat asthma, inflammatory bowel disease, rhinitis, pancreatits, cystitis (interstitial cystitis), uveitis, inflammatory skin disorders, rheumatoid arthritis and edema resulting from trauma associated with burns, sprains or fracture by the administration of a tablet, cachet, or capsule each containing, for example, 0.1 mg 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used subsequent to surgical intervention (e.g. as post-operative analgesics) and to treat inflammatory pain of varied origins (e.g. osteoarthritis, rheumatoid arthritis, rheumatic disease, teno-synovitis and gout) as well as for the treatment of pain associated with angina, menstruation or cancer by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used to treat diabetic vasculopathy, post capillary resistance or diabetic symptoms associated with insulitis (e.g. hyperglycemia, diuresis, proteinuria and increased nitrite and kallikrein urinary excretion) by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or tree times a day, or (in an extended release formulation) once, twice or three times a week.

They may be used to treat inflammatory skin disorders such as psoriasis and eczema by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used as smooth muscle relaxants for the treatment of spasm of the gastrointestinal tract or uterus or in the therapy of Crohn's disease, ulcerative colitis or pancreatitis by the administration of a tablet, cachet, or capsule each containing, for example, 0.1 mg 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Such compounds may be used therapeutically to treat hyperreactive airways and to treat inflammatory events associated with airways disease e.g. asthma, and to control, restrict or reverse airways hyperreactivity in asthma by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used to treat intrinsic and extrinsic asthma including allergic asthma (atopic or non-atopic) as well as exercise-induced broncho-constriction, occupational asthma, viral or bacterial exacerbated asthma, other non-allergic asthmas and "wheezy-infant syndrome" by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may also be effective against pneumoconiosis, including aluminosis, anthracosis, asbestosis, chalicosis, ptilosis, siderosis, silicosis, tabacosis and byssinosis was well as adult respiratory distress syndrome, chronic obstructive pulmonary or airways disease, bronchitis, allergic rhinitis, and vasomotor rhinitis by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Additionally, they may be effective against liver disease, multiple sclerosis, atherosclerosis, Alzheimer's disease, septic shock e.g. as anti-hypovolemic and/or anti-hypotensive agents, cerebral edema, headache including cluster headache, migraine including prophylactic and acute use, closed head trauma, irritable bowel syndrome and nephritis by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: (1) morphine and other opiate receptor agonists including propoxyphene (Darvon); (2) non-steroidal antiinflammatory drugs (NSAIDs) including COX-2 inhibitors such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone), and the coxibs (celecoxib, valecoxib, rofecoxib and etoricoxib); (3) corticosteroids such as betamethasone, budesonide, cortisone, dexamethasone, hydrocortisone, methylprednisolone, prednisolone, prednisone and triamcinolone; (4) histamine H1 receptor antagonists such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, desloratadine, foxofenadine and levocetirizine; (5) histamine H2 receptor antagonists such as cimetidine, famotidine and ranitidine; (6) proton pump inhibitors such as omeprazole, pantoprazole and esomeprazole; (7) leukotriene antagonists and 5-lipoxygenase inhibitors such as zafirlukast, montelukast, pranlukast and zileuton; (8) drugs used for angina, myocardial ischemia including nitrates such as nitroglycerin and isosorbide nitrates, beta blockers such as atenolol, metoprolol, propranolol, acebutolol, betaxolol, bisoprolol, carteolol, labetalol, nadolol, oxprenolol, penbutolol, pindolol, sotalol and timolol, and calcium channel blockers such as diltiazam, verapamil, nifedipine, bepridil, felodipine, flunarizine, isradipine, nicardipine and nimodipine; (9) incontinence medications such as antimuscarinics, e.g., tolterodine and oxybutinin); (10) gastrointestinal antispasmodics (such as atropine, scopolamine, dicyclomine, antimuscarinics, as well as diphenoxylate); skeletal muscle relaxants (cyclobenzaprine, carisoprodol, chlorphenesin, chlorzoxazone, metaxalone, methocarbamol, baclofen, dantrolene, diazepam, or orphenadrine); (11) gout medications such as allopurinol, probenicid and colchicine; (12) drugs for rheumatoid arthritis such as methotrexate, auranofin, aurothioglucose and gold sodium thiomalate; (13) drugs for osteoporosis such as alendronate and raloxifene; decongestants such as pseudoephedrine and phenylpropanolamine; (14) local anesthetics; (15) anti-herpes drugs such as acyclovir, valacyclovir and famcyclovir, and (15) anti-emetics such as ondansetron and granisetron.

Biological Evaluation
Assessing the Affinity of Selected Compounds to Bind to the Bradykinin B1 or B2 Receptor Radioligand binding assays are performed using membranes from CHO cells that stably express the human, rabbit, rat, or dog B1 receptors or CHO cells that express the human B2 receptor. For all receptor types, cells are harvested from culture flasks in PBS/1 mM EDTA and centrifuged at 1000×g for 10 minutes. The cell pellets are homogenized with a polytron in ice cold 20 mM HEPES, 1 mM EDTA, pH 7.4 (lysis buffer) and centrifuged at 20,000×g for 20 minutes. The membrane pellets are rehomogenized in lysis buffer, centrifuged again at 20,000×g and the final pellets are resuspended at 5 mg protein/ml in assay buffer (120 mM NaCl, 5 mM KCl, 20 mM HEPES, pH 7.4) supplemented with 1% BSA and frozen at −80° C.

On the day of assay, membranes are centrifuged at 14,000×g for 5 minutes and resuspended to the desired protein concentration in assay buffer containing 100 nM enaliprilat, 140 $\mu$g/mL bacitracin and 0.1% BSA. 3H-des-arg10, leu9 kallidin is the radioligand used for the human and rabbit B1 receptors, 3H -des-arg10 kallidin is used for the rat and dog B1 receptors, and 3H-bradykinin is used to label the human B2 receptor.

For all assays, compounds are diluted from DMSO stock solutions with 4 $\mu$L added to assay tubes for a final DMSO concentration of 2%. This is followed by the addition of 100 $\mu$L radioligand and 100 $\mu$L of the membrane suspension. Nonspecific binding for the B1 receptor binding assays is determined using 1 $\mu$M des-arg10 kallidin and nonspecific binding for the B2 receptor is determined with 1 $\mu$M bradykinin. Tubes are incubated at room temperature (22° C.) for 60 minutes followed by filtration using a Tomtec 96-well harvesting system. Radioactivity retained by the filter is counted using a Wallac Beta-plate scintillation counter.

The compounds of this invention have affinity for the B1 receptor in the above assay as demonstrated by results of less than 5 $\mu$M. It is advantageous that the assay results be less than 1 $\mu$M, even more advantageous for the results be less than 0.5 $\mu$M. It is further advantageous that compounds of this invention have affinity for the bradykinin B1 receptor over the bradykinin B2 receptor, more advantageously, the affinity for the B1 receptor is at least 10 fold, and preferably over 100 fold, over that for the B2 receptor.

Assay for Bradykinin B1 Antagonists

B1 agonist-induced calcium mobilization was monitored using a Fluorescence Imaging Plate Reader (FLIPR). CHO cells expressing the B1 receptor were plated in 96 or 384 well plates and allowed to incubate in Iscove's modified DMEM overnight. Wells were washed two times with a physiological buffered salt solution and then incubated with 4 uM Fluo-3 for one hour at 37° C. The plates were then washed two times with buffered salt solution and 100 uL of buffer was added to each well. Plates were placed in the PLIPR unit and allowed to equilibrate for two minutes. The test compound was then added in 50 ul volumes followed five minutes later by 50 ul of agonist (des-arg$^{10}$ kallidin). Relative fluorescence peak heights in the absence and presence of antagonist were used to calculate the degree of inhibition of the B1 receptor agonist response by the test compound. Eight to ten concentrations of test compound were typically evaluated to construct an inhibition curve and determine IC50 values using a four-parameter nonlinear regression curve fitting routine.

Assay for Bradykinin Inverse Agonists

Inverse agonist activity at the human B1 receptor was evaluated using transiently transfected HEK293 cells. One day following transfection cell flasks were labeled overnight with 6 uCi/ml [$^3$H]myo-inositol. On the day of assay, the media was removed and the attached cells were gently rinsed with 2×20ml of phosphate-buffered saline. Assay buffer (HEPES buffered physiological salts, pH 7.4) was added and the cells were detached by tapping of the flask. The cells were centrifuged at 800×g for five minutes and resuspended at 1×10$^6$ cells/ml in assay buffer supplemented with 10 mM lithium chloride. After 10 minutes at room temperature, one-half ml aliquots were distributed to tubes containing test compound or vehicle. After an additional 10 minutes the tubes were transferred to a 37° C. water bath for 30 minutes. The incubation was terminated by the addition of a 12% perchloric acid solution and the tubes were placed on ice for 30 minutes. The acid was then neutralized with KOH and the tubes centrifuged to pellet precipitated material. [$^3$H]Inositol monophosphate formed was recovered by standard ion exchange chromatographic techniques and quantitated by liquid scintillation counting. Inverse agonist activity was determined by the degree to which a test compound reduced basal (cells incubated with vehicle) levels of [$^3$H]inositol monophosphate accumulation.

Ex vivo Receptor Occupancy Assay in NSE hB$_1$ Transgenic Rat

Transgenic rats of either sex are placed in an induction chamber and anesthetized with isoflurane under a Flow Sciences hood. Once anesthetized, the rat is placed on a circulating water warming blanket (Gaymar T-pump) and anesthesia is maintained using 2% isoflurane by means of a nose cone. The tail vein is cannulated with a 25 G winged infusion set-up connected to a syringe containing either test compound or vehicle. The desired dose of test compound is administered. At the experimental end-point a blood sample is taken, the rat is euthanized, and tissue is removed (typically brain and spinal cord) for subsequent assays.

For autoradiographic analysis of human B$_1$ receptor expression, tissues removed from transgenic rats were frozen on dry ice powder, and stored at −70° C. Coronal sections of the brain and the transverse sections of the spinal cord were prepared with cryostat (Leica, CM3050) at 20 $\mu$M of each. The frozen sections were stored at −70° C. For analysis, frozen sections were warmed at room temperature (RT) for 15 minutes, then followed by 15 minutes preincubation in the buffer without radoligand at RT. After preincubation, the sections were transferred to the incubation buffer, and incubated for 90 minutes at RT. Total binding, both non-specific and specific, was determined by incubating in buffer containing 0.3 nM [H-3] DALK. An adjacent section was utilized to determine nonspecific binding, which was incubated in buffer containing 0.3 nM [H-3] DALK and 200 nM of a non-peptide receptor antagonist that exhibits high affinity and specificity for the human B$_1$ bradykinin receptor. Following the 90 minute incubation, the sections were washed three times, 3 minutes each, in buffer, rinsed in DIH$_2$O for 30 seconds at 4° C., and then dried by air blower at RT. The sections were placed against Fuji imaging plates, and exposed for a week at RT. The plates were scanned with Fuji PhosphorImager BAS 5000, and the images were analyzed with MCID M5 software.

For homogenate-based binding assay, thirty-five milligrams of frozen brain (cerebral cortex or cerebellum) or spinal cord is homogenized with a Polytron, in a large volume of ice-cold assay buffer (20 mM HEPES, 120 mM NaCl, 5 mM KCl, pH 7.4) and transferred to two chilled centrifuge tubes. To pellet membranes the tubes are centrifuged for 10 minutes at 75,000×g in a rotor pre-cooled to 4° C. The supernatant is discarded and each tube is rinsed with 20 ml ice-cold buffer and then homogenized pellets above in ice-cold assay buffer. The homogenate is pooled and added to a tube containing the radiotracer, 20 pM of a non-peptide human $B_1$ receptor antagonist that is labeled with $^{35}S$, in each tube containing 0.5 ml room temperature assay buffer. Nonspecific binding is determined by adding homogenate to tubes containing the radiotracer and 100 nM of the unlabeled non-peptide human $B_1$ receptor antagonist. At set time points (1,2,4,6,8,10 minutes) the contents of three tubes are filtered over individual 25 mm GF/B filters presoaked in 0.05% Triton X-100. The filtration step is performed by adding 4 ml ice-cold assay buffer to each of the three replicate tubes, pouring the contents over the filters, and washing each filter two times with 4 ml ice-cold buffer. A Hoeffer FH 225V filtration manifold is used for the filtration. The nonspecific binding tubes are similarly filtered after finishing the 6 time points. Filters are transferred to 5 ml scintillation vials and counted after soaking 10 hours in 3 ml Beckman Ready Safe scintillation fluid.

The specific binding is calculated at each time point (total cpm—nonspecific cpm) and the slope of the association is determined by linear regression. Receptor occupancy in a drug treated animal is determined by the following equation:

% Occupancy=(1−(slope$_{drug}$/slope$_{vehicle}$))×100 slope$_{drug}$ is the slope of the association rate line from a drug treated animal.
slope$_{vehicle}$ is the slope determined for a vehicle treated animal.

The transgenic rat expressing human badykinin B1 receptor is described in PCT Published Application WO03/016495.

Abbreviations Used

The following abbreviations have the meanings indicated, unless stated otherwise in the specification:

| | |
|---|---|
| BOC (boc) | t-butyloxycarbonyl |
| DCM | dichloromethane |
| DMF | dimethylformamide |
| DMSO | Dimethyl sulfoxide |
| EDC or EDCI | 1-(3-dimethylaminopropyl)3-ethylcarbodiimide HCl |
| eq. | equivalent(s) |
| ES (or ESI) - MS | electron spray ionization - mass spectroscopy |
| Et | ethyl |
| EtOAc | ethyl acetate |
| EtOH | ethanol |
| FAB-MS | fast atom bombardment-mass spectroscopy |
| HOBt | 1-hydroxybenzotriazole hydrate |
| HPLC | high pressure liquid chromatography |
| LCMS | Liquid chromatography/mass spectroscopy |
| LHMDS | lithium bis(trimethylsilyl)amide |
| Me | methyl |
| MeOH | Methanol |
| MHz | megahertz |
| MsCl | Mesyl chloride |

-continued

| | |
|---|---|
| NEt$_3$ | Triethylamine |
| NMR | nuclear magnetic resonance |
| TFA | trifluoroacetic acid |
| THF | tetrahydrofuran |

Compounds of formula I may be prepared according to the following illustrative schemes.

The construction of the 2-qiuinoxalinone core is illustrated in Scheme I. An α-amino acid 1 and 2-fluoronitrobenzene 2 are reacted in the presence of sodium bicarbonate followed by HCl to provide the N-arylamino acid 3. Treatment of 3 with hydrogen gas or otin chloride provides the quinoxalinone 4, which may be treated with $R^{4'}$-L to provide the (amide) N-substituted quinoxalinone 5; L is a suitable leaving group such as halide and sulfonate.

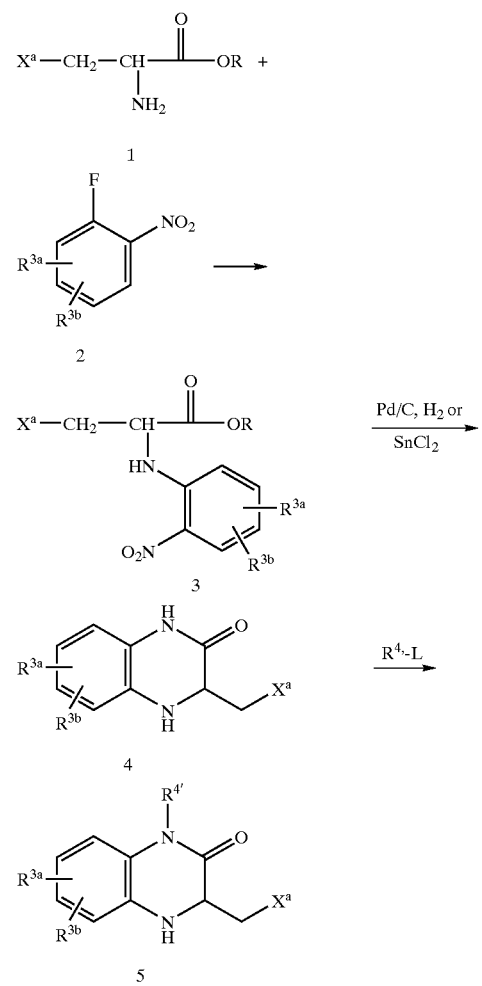

The quinoxalinones 4 and 5 may be further elaborated to provide intermediates for the preparation of compounds of formula I as shown in Scheme 2. Thus, compound 6 where R is an ester may be hydrolyzed to provide the corresponding carboxylic acid 8. Compound 6 may also be reduced using e.g. a lithium aluminum hydride reagent such as LiAlH(tBuO)$_3$ to give the corresponding alcohol 7.

Scheme 2

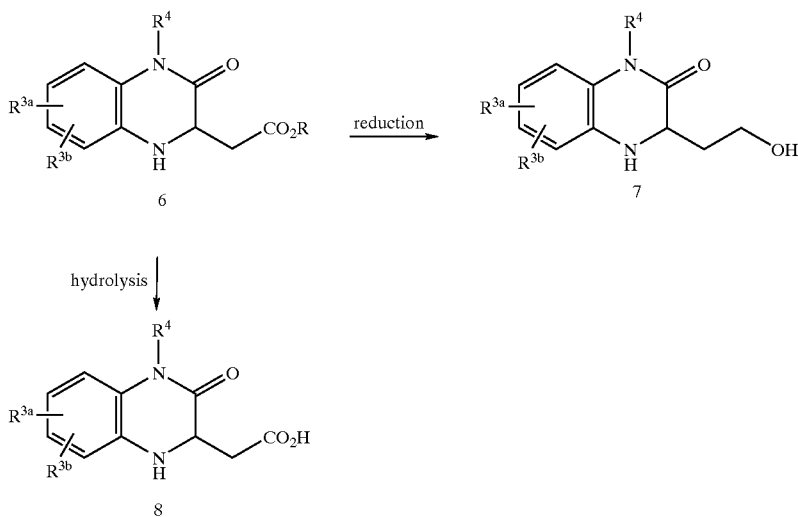

3-Hydroxyalkyl-2-quinoxalinone 9 may be further elaborated to provide suitable intermediates as shown in Scheme 3. The hydroxy group is converted to the mesylate 10 using mesyl chloride. Treatment of the mesylate with sodium azide provides the corresponding azido derivative 12, which upon hydrogenation, gives the amine compound 14. Treatment of the mesylate 10 with potassium thioacetate gives the thioate 11, which upon hydrolysis, yields the corresponding thiol 13.

Scheme 3

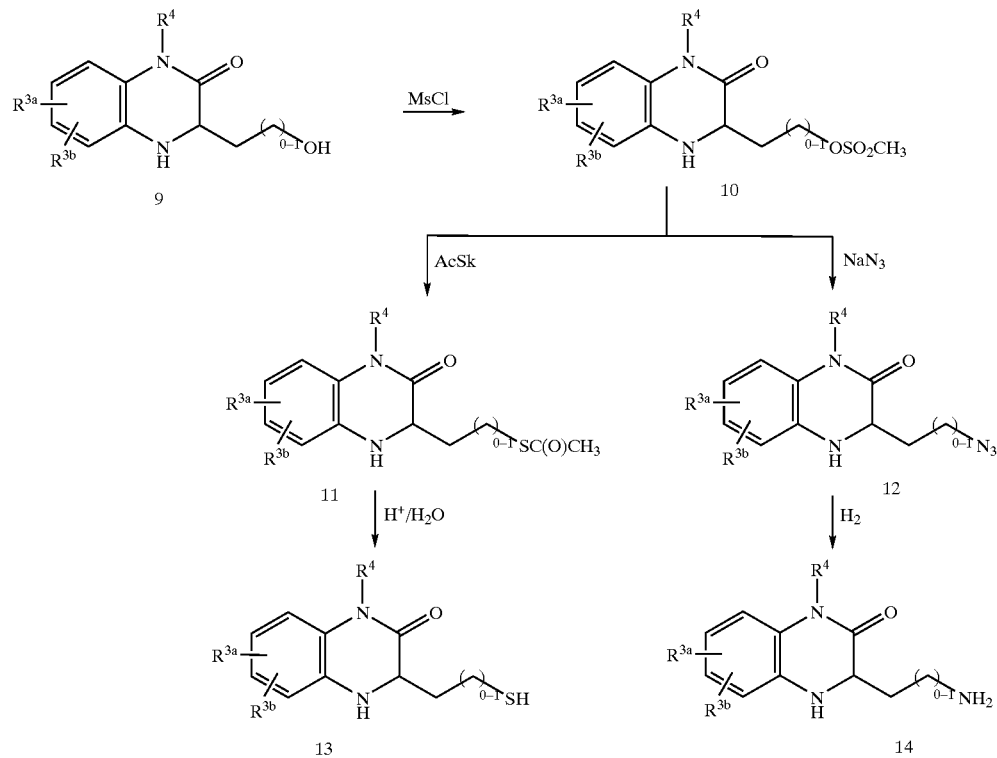

Derivatization of the various functional groups of compounds 8–14 to provide compounds of formula I illustrated in Scheme 4. The reactions such as amide and ester bond formation, nucleophilic substitution, oxidations may be achieved using conventional synthetic methods well known in the art. Compound 15 may react with $R^2$—Y-L, where L is a suitable leaving group such as halide to provide 16, which is then subject to derivatization at the 3-sidechain of quinoxaline to provide 16a–16e; or alternatively, derivatization at the 3-sidechain is performed first to provide compounds 15a–15e, which are then treated with $R^2$—Y-L to provide the corresponding 16 compound.

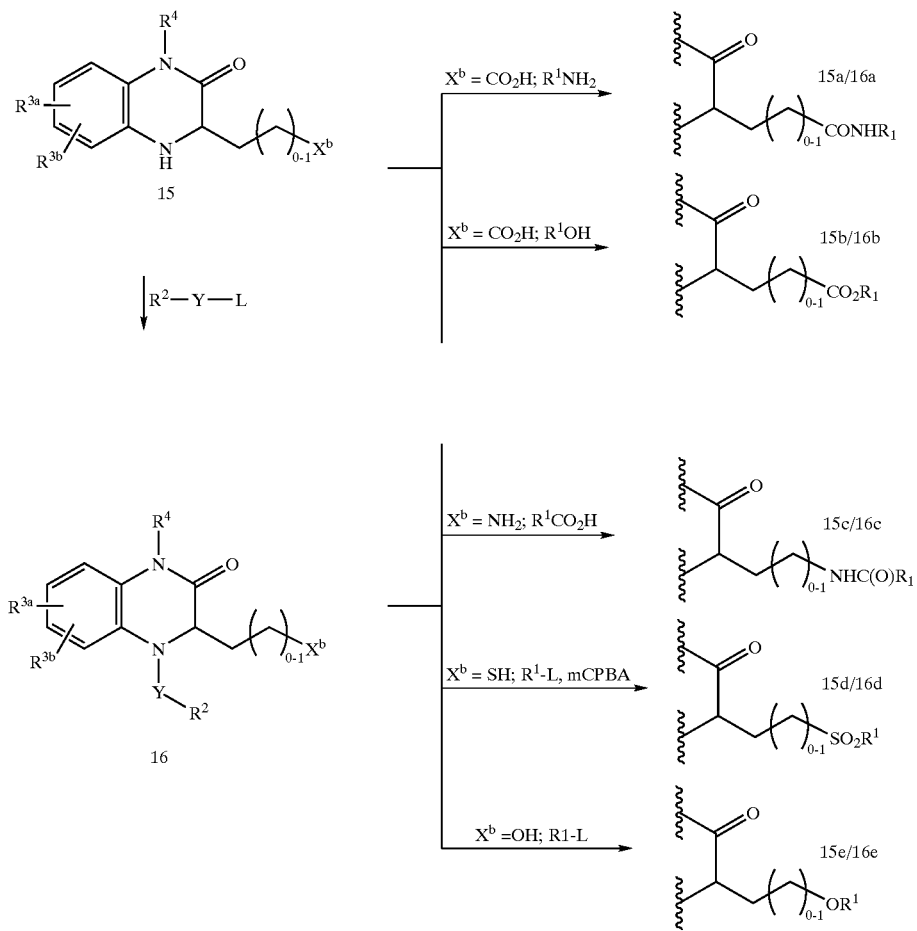

Scheme 4

As illustrated in Scheme 5, 3-allyl-quinoxalinone 17 or 18 may be reacted with an alkene in the presence of Grubb's catalyst to provide the corresponding unsaturated compound 17a or 18a, which upon hydrogenation, provides the saturated compound 17b or 18b, respectively.

Scheme 5

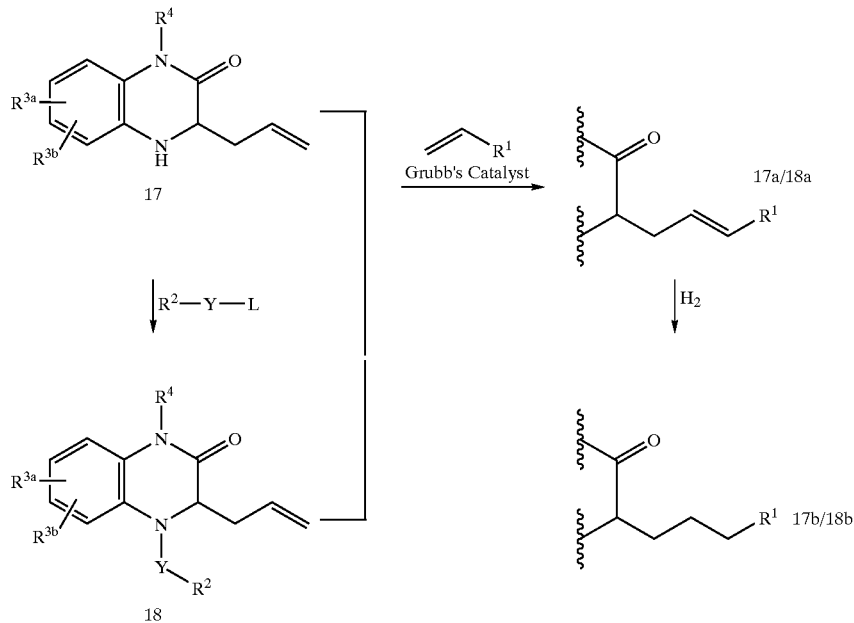

REFERENCE EXAMPLES (1) Preparation of 4-(2-aminoethyl)benzonitrile

To a solution of 4-(2-hydroxyethyl)benzonitrile (10.0 g, 67.94 mmol) in $CH_2Cl_2$ (175 mL) at 0° C. was added $Et_3N$ (11.36 mL, 8.25 mmol) and MsCl (6.31 mL, 81.53 mmol). After stirring at 0° C. for 3.5 hours, the reaction was poured into water (100 ml) and separated. Organic layer was dried over $Na_2SO_4$, filtered and concentrated in vacuo. Crude residue was dissolved in DMF (100 mL) and $NaN_3$ (9.15 g, 140.72 mmol) and water (5 mL) were added. The resulting solution was heated to 125° C. After overnight stirring at 125° C., the crude reaction mixture was cooled, diluted with EtOAc (200 mL) and poured into water (150 mL). Organic layer was washed with water (5×150 mL), dried over sodium sulfate, filtered, and concentrated to give 4-(2-azidoethyl) benzonitrile which was used without purification.

A solution of 4-2-azidoethyl)benzonitrile (500 mg, 2.90 mmol) in 1:1 EtOH/EtOAc (3 mL) at 0° C. was purged with $N_2$. Then Pd/C (440 mg) was added and a $H_2$ balloon was placed over the reaction. After stirring at 0° C. for two hours, the reaction mixture was filtered through a pad of celite and concentrated to give 4-(2-aminoethyl)benzonitrile, which was used without further purification. LCMS (ES) 147.3 m/z $(M+H)^+$.

(2) Preparation of 2-[4-(4,5-dihydro-1H-imidazol-2-yl) phenyl]ethanamine

A solution of 4-(2-azidoethyl)benzolnitrile (10.65 g, 172.19 mmol) in EtOAc (250 mL) at 0° C. was bubbled with $HCl_{(g)}$ until saturation. Reaction was sealed and allowed to warm to room temperature slowly. After overnight stirring, the crude reaction mixture was concentrated under reduced pressure. The residue (10.1 g, 46.28 mmol) was taken up in EtOH and ethylene diamine (6.19 mL, 92.55 mmol) was added. After overnight stirring, the crude reaction mixture was concentrated, diluted with EtOAc (200 mL) and washed with water (3×150 mL). Organic layer was dried over sodium sulfate, filtered, and concentrated. Crude product was purified by flash chromatography on silica gel eluting with 10%–20% MeOH in $CHCl_3$ with 1% $NH_4OH$ to give 900 mg (9%) of 2-[4-(4,5-dihydro-1H-imidazol-2-yl) phenyl]-ethanmine. LCMS (ES) 216.3 m/z $(M+H)^+$.

(3) Preparation of 4-(4,5-dihydro-1H-imidazol-2-yl)phenyl] acetic Acid

To a solution of 4-(2-hydroxyethyl)benzonitrile (120 mg, 0.816 mmol) in acetone (3 mL), Jone's reagent (1.5 mL, 4.005 mmol) was added. After stirring for 10 minutes at room temperature, the crude reaction mixture was poured into water (10 mL) and extracted with $CHCl_3$ (6×10 mL). Combined organics were dried over magnesium sulfate, filtered, and concentrated to give (4-cyanophenyl)acetic acid which was used without purification.

To a solution of (4-cyanophenyl)acetic acid (131 mg, 0.816 mmol) in EtOH (0.5 mL) at 0° C. was bubbled $HCl_{(g)}$ until saturation. Reaction mixture was allowed to warm to room temperature slowly. After overnight stirring, the crude reaction mixture was concentrated in vacuo. This residue was taken up in EtOH (4 mL) and ethylene diamine (0.1 mL, 1.49 mmol) was added. After stirring at room temperature for two hours, the crude reaction mixture was concentrated under reduced pressure and then re-dissolved in DMF (2 mL). To this solution was added 1M NaOH (2 mL, 2 mmol) and the reaction stirred at room temperature for three hours. Crude reaction mixture was neutralized with 1M HCl to a pH 6 and extracted with $CHCl_3$ (4×15 mL). Product was found in the water layer, so combined all layers and concentrated in vacuo, re-dissolved in $CHCl_3$/MeOH, and filtered to remove precipitate. Concentration of the filtrate gives [4-(4,5-dihydro-1H-imidazol-2-yl)phenyl]acetic acid, which was used without further purification. LCMS (ES) 205.1 m/z $(M+H)^+$ (4) Preparation of 4-(3-iodopropyl)benzonitrile To a solution of 4-(3-hydroxyprop-1-ynyl)benzonitrile (2.0 g, 12.7 mmol) in EtOAc (25 mL), Pd/C (500 mg, 0.47 mmol) was added. A hydrogen balloon was placed over the reaction, and the reaction stirred for approximately four hours. An additional 200 mg (0.19 mmol) of Pd/C was added and the balloon was placed back over the reaction. Upon completion, the reaction mixture was filtered through a pad of celite and concentrated to give 4-(3-hydroxypropyl) benzonitrile which was used without further purifications.

To a solution of 4-(3-hydroxypropyl)benzonitrile (1.8 g, 11.2 mmol) in $CH_2Cl_2$ (50 mL) at 0° C., $Et_3N$ (1.06 mL, 13.4 mmol) and then MsCl (0.95 mL, 12.5 mmol) were added. Upon completion, the reaction mixture was poured into 0.5M HCl and extracted with EtOAc. The crude mesylate was dissolved in acetone and treated with NaI (3.0 g, 20.0 mmol) in the dark at room temperature. When complete, the reaction was purified by flash chromatography on silica gel eluting with 15% EtOAc in Hexanes to afford the title compound.

(5) Preparation of 2-[4-(1H-imidazol-2-yl)phenyl] ethanamine

A solution of 4-(2-azidoethyl)benzonitrile (2.0 g, 11.62 mmol) in EtOH (50 ml) at 0° C. was saturated with $HCl_{(g)}$. Reaction mixture was allowed to warm to room temperature and stirred overnight. Concentration of the crude reaction mixture gave ethyl 4-(2-azidoethyl)benzenecarboximidoate which was used without further purification.

Ethyl 4-(2-azidoethyl)benzenecarboximidoate (3.17 g, 14.55 mmol) and dimethylanoacetal (1.90 ml, 17.46 mmol) were mixed together in EtOH (20 mL) at room temperature. After 2.5 hours, 7 mL of HOAc were added. After overnight stirring, the reaction was heated to 50° C. and stirred for 3.5 hours before 1 mL of water was added. After an additional three hours of stirring at 50° C., the crude reaction mixture was diluted with EtOAc (200 mL) and washed with 10% $Na_2CO_3$ (2×50 mL) and brine (1×50 mL). The crude residue was taken up in water (20 mL) and concentrated HCl was added (20 mL). Resulting solution stirred at room temperature for three hours and was then heated to 80° C. for an additional one hour. Reaction mixture was cooled and $K_2CO_3$ (solid) was added until bubbling was no longer apparent upon addition. Crude material was extracted with $CH_2Cl_2$ (4×50 mL), dried over sodium sulfate, filtered, and concentrated. Purification by flash chromatography on silica gel eluting with 1%–5% MeOH in $CH_2Cl_2$ gave 910 mg (29%) of 2-[4-(2-azidoethyl)phenyl]-1H-imidazole.

To a solution of 2-[4-(2-azidoethyl)phenyl]-1H-imidazole (120 mg, 0.56 mmol) in EtOH, Pd/C (6 mg, 0.06 mmol) was added. A hydrogen balloon was placed over the reaction and the reaction was complete after approximately five hours. Reaction mixture was filtered through a pad of celite and concentrated to give 2-[4-(1H-imidazol-2-yl)phenyl] ethanamine which was used without further purification. LCMS (ES) m/z 188.4 $(M+H)^+$.

(6) Preparation of 2-[4-(1H-imidazol-1-yl)phenyl] ethanamine

Tert-butyl 2-(4-bromophenyl)ethylcarbamate (500 mg, 1.67 mmol), imidazole (170 mg, 2.50 mmol), $(CuOTf)_2 \cdot PhH$ (84 mg, 0.17 mmol), 1,10-Phenanthroline (360 mg, 2.00 mmol), dba (39 mg, 0.17 mmol), and $Cs_2CO_3$ (650 mg, 1.99 mmol) were mixed together in a flask and o-xylene (10 mL) was added. Resulting solution was heated to 120° C. and stirred for four days. Reaction mixture was then cooled, poured into water (20 mL) and extracted with EtOAc (3×20 mL). Combined organics were washed with water (1×20 mL) and brine (2×20 mL), dried over sodium sulfate, filtered, and concentrated Crude product was purified by flash chromatography eluting with 25% Hexanes in EtOAC to pure EtOAc to give tert-butyl 2-[4-(1H-imidazol-1-yl) phenyl]ethylcarbamate.

$HCl_{(g)}$ was bubbled into a solution of tert-butyl 2-[4-(1H-inidazol-1-yl)phenyl]ethylcarbamate in EtOAc cooled to 0° C. until saturated. Reaction stirred for one hour at 0° C. and was then concentrated to give 2-[4-(1H-imidazol-1-yl) phenyl]-ethanamine, which was used without further purification. LCMS (ES) 188.3 m/z $(M+H)^+$.

(7) Preparation of 2-[4-(4H-1,2,4-triazol-4-yl)phenyl] ethanane

To a solution of tert-butyl 2-(4-aminophenyl) ethylcarbamate (200 mg, 0.85 mmol) in Toluene (2 mL) was added N,N-dimethylformamide azine (120 mg, 0.85 mmol, prepared by the method described in *Bioorg. Med. Chem. Letters*, 6(15): 1825–1830, 1996) and $TsOH \cdot H_2O$ (16 mg, 0.08 mmol). Resulting solution was heated to reflux and stirred overnight. Reaction mixture was cooled, concentrated in vacuo, and subjected to silica gel chromatography eluting with 2%–5% MeOH in $CH_2Cl_2$ to give 250 mg (100%) tert-butyl 2-[4-(4H-1,2,4txiazol-4-yl)phenyl] ethylcarbamate. LCMS (ES) 289.3 m/z $(M+H)^+$.

A suspension of tert-butyl 2-[4(4H-1,2,4-triazol-4-yl) phenyl]ethylcarbamate (250 mg, 0.87 mmol) in EtOAc (4 mL) at 0° C. was saturated with $HCl_{(g)}$. After stirring at 0° C. for two hours, the reaction was concentrated to give 2-[4-(4H-1,2,4-triazol-4-yl)phenyl]ethanamine, which was used without further purification. LCMS (ES) 189.3 m/z $(M+H)^+$.

(8) Preparation of 4-(2-aminoethyl)benzamide

To a solution of 4-(2-azidoethyl)benzonitrile (1.0 g, 5.81 mmol) in a 5:1 mixture of $MeOH/H_2O$ (100 mL), $K_2CO_3$ (4.41 g. 31.94 mmol) was added and the resulting solution cooled to 0° C. Then 15.4 mL of a 30% $H_2O_2$ solution was added and the reaction was allowed to warm to room temperature. After stirring at room temperature for approximately three hours, the crude reaction mixture was concentrated under reduced pressure to remove MeOH and then extracted with EtOAc (3×100 mL). Combined organics were dried over sodium sulfate, filtered, and concentrated in vacua. Crude product was subjected to silica gel purification eluting with 1% MeOH in $CH_2Cl_2$ to give 1.06 g (96%) of 4-(2-azidoethyl)benzamide.

Pd/C (11 mg, 0.11 mmol) was added to a solution of 4-(2-azidoethyl)benzamide (200 mg, 1.05 mmol) in EtOH (4 mL). A hydrogen balloon was placed over the reaction and it stirred for about four hours. The crude reaction was filtered through a pad of celite and concentrated to give 4-(2-aminoethyl)benzamide which was used without further purification.

EXAMPLE 1

2-{1-[(2R)-(3,4-dichlorophenyl)sulfonyl]-3-oxo-1,2, 3,4-tetrahydroquinoxalin-2-yl}-N-{2-[4-(4,5 -dihydro-1H-imidazol-2-yl)phenyl]ethyl}acetamide

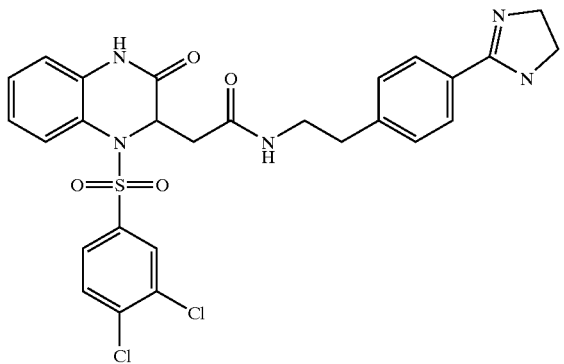

Step 1; To a solution of dimethyl D-aspartate (18 g, 111.7 mmol) in MeOH (500 mL) was added 2-fluoronitrobenzene (17.33 g, 122.86 mmol) and NaHCO$_3$ (9.38 g, 111.7 mmol). Reaction mixture was refluxed under N$_2$ for ~2 days. The solvent was removed under reduced pressure and the residue chased with benzene (2×100 mL). Crude material was then redissolved in 200 mL of MeOH (200 mL), cooled to 0° C. and brought to a pH of ~4 by bubbling in HCl(g). Reaction mixture stirred overnight at room temperature and concentrated under reduced pressure. The residue was taken up in EtOAc and washed with sat NaHCO$_3$/10% Na$_2$CO$_3$ (9:1) (2×500 mL) and once with brine (1×300 mL). Organic layer was dried over sodium sulfate, filtered, and concentrated to give dimethyl (2S)-2-[(2-nitrophenyl)amino]butanedioate (25.54 g, 81%). LCMS (ES) 283.0 m/z (M+H)$^+$.

Step 2: To solution of dimethyl (2S)-2-[(2-nitrophenyl)amino]butanedioate (954 mg, 3.38 mmol) in EtOH (200 mL) was added 10% Pd/C (36 mg, 3.38 mmol) and then placed on Parr Hydrogenator for two days. Filtering crude material through a pad of celite and concentrating in vacuo gave methyl {(2R)-3-oxo-1,2,3,4-tetrahydroquinoxalin-2-yl}acetate (727 mg, 98%) which was used without further purification. LCMS (ES) m/z 221.25 (M+H)$^+$.

Step 3: To a solution of methyl {(2R)-3-oxo-1,2,3,4tetrahydroquinoxalin-2-yl}acetate (727 mg, 3.3 mmol) in pyridine (5 mL) at room temperature was added 3,4-dichlorobenzenesulfonyl chloride (1.03 mL, 6.6 mmol). The resulting solution was stirred at room temperature overnight. Pyridine was removed in vacuo and crude material was purified by flash chromatography on silica gel eluting with a 25-50% EtOAc:hexanes gradient to give methyl {(2R)-1-[(3,4-dichlorophenyl)sulfonyl]-3-oxo-1,2,3,4-tetrahydroquinoxalin-2-yl}acetate (698 mg, 49%). LCMS (ES) m/z 429.1.

Step 4: A solution of methyl {(2R)-1-[(3,4-dichlorophenyl)sulfonyl]-3-oxo-1,2,3,4-tetrahydroquinoxalin-2-yl}acetate (698 mg, 1.63 mmol) in 1M HCl (20 mL) was refluxed overnight. The reaction mixture was concentrated under reduced pressure and dried on the high vacuum pump to give {(2R)-1-[(3,4-dichlorophenyl)-sulfonyl]-3-oxo-1,2,3,4-tetrahydroquinoxalin-2-yl}acetic acid (561 mg) that was taken on to the next step without purification. LCMS (ES) m/z 415.1.

Step 5: To a solution of {(2R)-1-[(3,4-dichlorophenyl)sulfonyl]-3-oxo-1,2,3,4-tetrahydroquinoxalin-2-yl}acetic acid (1.3 g, 3.13 mmol) in CH$_2$Cl$_2$ (10 mL) at room temperature was added Et$_3$N (1.31 mL, 9.39 mmol) followed by EDCI (1.2 g, 6.26 mmol), HOAt (852 mg, 6.26 mmol), and 4-(2-aminoethyl)benzonitrile (915 mg, 6.26 mmol). After stirring overnight at room temperature, the reaction mixture was diluted with CH$_2$Cl$_2$ (40 mL) and water (50 mL) and then extracted with CH$_2$Cl$_2$ (3×50 mL). Combined organic layers were dried over sodium sulfate, filtered, and evaporated under reduced pressure. Crude product residue was subjected to silica gel chromatography eluting with 5% MeOH in CH$_2$Cl$_2$ to give 985 mg (58%) of N-[2-(4-cyanophenyl)ethyl]-2-{(2R)-1-[(3,4dichlorophenyl)sulfonyl]-3-oxo-1,2,3,4-tetrahydroquinoxalin-2-yl}acetamide. $^1$H NMR (CDCl$_3$) δ 7.64 (d, J=8.05 Hz, 2H), 7.57 (d, J=8.05, 1H), 7.46 (d, J=8.32 Hz, 1 H), 7.44 (d, J=2.19 Hz, 1H), 7.36 (d, J=8.22 Hz, 2H), 7.27-7.31 (m, 2H), 7.18 (t, J=7.73 Hz, 1H), 6.72 (d, J=7.95 Hz, 1H), 5.95 (bt, 1H), 5.11 (dd, J=9.97, 4.39 Hz, 1H), 3.56 (dd, J=13.71, 6.22 Hz, 2H), 2.94 (t, J=7.04 Hz, 2H), 2.53 (dd, J=15.36, 4.48, 1H), 2.34 (dd, J=15.50, 9.92 Hz, 1H); MS (ES) m/z 543.1.

Step 6: To a solution of N-[2-4-cyanophenyl)ethyl]-2-{(2R)-1-[(3,4-dichloro-phenyl)sulfonyl]-3oxo-1,2,3,4-tetrahydroquinoxalin-2-yl}acetamide (985 mg, 1.81 mmol) in EtOH (100 mL) at 0° C. was bubbled HCl(g) for ~10 minutes. Reaction mixture was then capped and allowed to warm to room temperature slowly. After overnight stirring, the reaction mixture was concentrated in vacuo. The residue was dissolved in EtOH and to this solution was added ethylene diamine (0.13 mL, 2.00 mmol). After overnight stirring, the solvent was removed in vacuo. The residue was taken up in CH$_2$Cl$_2$ and poured into water. Water layer was extracted with CH$_2$Cl$_2$ (2×100 mL). Combined organic layers were washed with brime (1×200 ml), dried over sodium sulfate, filtered, and concentrated. Crude material was subjected to silica gel chromatography eluting first with 20% MeOH in CH$_2$Cl$_2$ then with 20% MeOH in CH$_2$Cl$_2$ with 1% NH$_4$OH to yield 541 mg of tide compound (51% overall yield for two steps). $^1$H NMR (400 MHz, CD$_3$OD) δ 7.79 (d, J=34.07 Hz, 2H), 7.63 (d, J=8.41 Hz, 1H), 7.51 (dd, J=7.96, 1.28 Hz, 1H), 7.44 (d, J=8.23 Hz, 2H), 7.41 (d, J=2.10 Hz, 1H), 7.30-7.34 (m, 2H), 7.16 (td, J=7.68, 1.37 Hz, 1H), 6.81 (dd, J=8.13, 1.46 Hz, 1H), 5.13 (q, J=4.94 Hz, 1H), 3.94 (s, 4H), 3.47-3.54 (m, 1H), 3.37-3.41 (m, 1H), 2.87-1.92 (m, 2H), 2.40 (dd, J=14.36, 4.67 Hz, 1H), 2.25 (dd, J=14.45, 4.30 Hz, 1H); MS (ES) m/z 586.22.

EXAMPLE 2

N-({(2R)-1-[(3,4-dichlorophenyl)sulfonyl]-3-oxo-1,2,3,4-tetrahydroquinoxalin-2-yl}methyl)-2-[4-(4,5-dihydro-1H-imidazol-2-yl)phenyl]acetamide

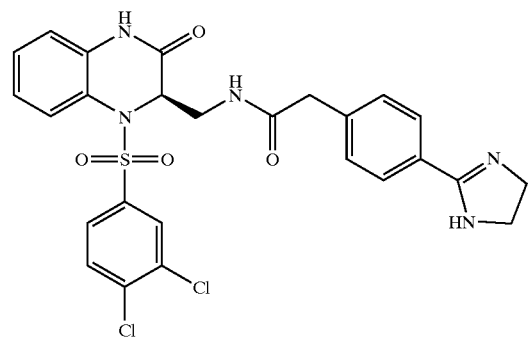

To a solution of BOC-O-benzyl-D-serine (5.05 g, 17.12 mmol) in MeOH (100 mL) at −78° C., was added SOCl$_2$ dropwise. The reaction mixture was warmed to 0° C. and stirred for ~4 hours and then concentrated. The residue was taken up in EtOAc and washed with 10% Na$_2$CO$_3$ (3×80 mL). The organic layer was dried over sodium sulfate, filtered and concentrated. To the crude material in EtOAc (100 mL) at 0° C. was bubbled HCl gas for approximately 10 minutes, and the reaction was capped and the mixture stirred at 0° C. for 30 minutes before it was concentrated in vacuo. The crude material was diluted with 50 mL of a 1:1 solution of saturated NaHCO$_3$/10% Na$_2$CO$_3$ and extracted with EtOAc (4×50 mL). The combined organics were dried over sodium sulfate, filtered, and concentrated to give O-benzyl-D-serine methyl ester (3.13 g, 14.96 mmol) which was used without further purification. LCMS (ES) m/z 210.1 (M+H)$^+$.

To a solution of O-benzyl-D-serine methyl ester (3,13 g, 14.96 mmol) in MeOH, was added 2-fluoronitrobenzene (1.6 mL, 15.08 mmol) and NaHCO$_3$ (1.3 g, 15.48 mmol), and the resulting solution was brought to a reflux for approximately one day. The reaction mixture was then cooled, filtered, concentrated and chased with benzene (4×50 ml). The residue was re-dissolved in EtOAc, cooled to 0° C. and HCl gas was bubbled into the resulting solution until it reached a pH of ~4. The reaction mixture was allowed to warm to room temperature and stirred for 5 hours. Upon completion, the reaction mixture was washed with saturated NaHCO$_3$ (3×50 mL), dried over sodium sulfate, filtered and concentrated under reduced pressure. The crude product was subjected to silica gel chromatography eluting with 8%–30% EtOAc in Hexanes to give 1.09 g (3.30 mmol) of N-(2-nitrophenyl)-O-benzyl-D-serine methyl ester.

To a solution of N-2-nitrophenyl)-O-benzyl-D-serine methyl ester (1.45 g, 4.39 mmol) in EtOH (50 mL) was added Pd/C (1.03 g, 96.71 mmol), and the resulting slurry was placed in a Parr hydrogenator at 55 psi overnight. The next morning, an additional 1.0 g (93.89 mmol) of Pd/C was added to the reaction mixture and it was placed back in the Parr hydrogenator for four days. The reaction mixture was filtered through celite and concentrated in vacuo. Flash chromatography on silica gel eluting with 50% EtOAc to 100% EtOAc in Hexanes gave the benzyl ether product and (3R)-3-(hydroxymethyl)-3,4-dihydroquinoxalin-2(1H)-one. LCMS (ES) m/z 179.1 (M+H)$^+$.

To a solution of (3R)-3-(hydroxymethyl)-3,4-hydroquinoxalin-2(1H)-one(157 mg, 0.88 mmol) in CH$_2$Cl$_2$ (5 mL) was added mesyl chloride (125 uL, 1.62 mmol), and Et$_3$N (370 uL, 2.65 mmol). The reaction mixture was stirred for one hour and was then poured into water and extracted with EtOAc (4×20 mL). The combined organics were then washed with brine (1×30 mL), dried over sodium sulfate and concentrated under reduced pressure. The crude residue was dissolved in DMF (2 mL), and NaN$_3$ (170 mg, 2.61 mmol) was added and the resulting solution was heated to 80° C. for 2 hours. The reaction mixture was cooled, diluted with EtOAc (100 mL) and washed with water (3×20 mL) and brine (1×20 mL). The organic layer was dried over sodium sulfate, filtered, concentrated to give (3R)-3-(azidomethyl)-3,4-dihydroquinoxalin-2(1H)-one, which was used without further purification.

To a solution of (3R)-3-(azidomethyl)-3,4-dihydroquinoxalin-2(1H)-one (122 mg, 0.60 mmol) in pyridine (3 mL) was added 3,4-dichlorobenzenesulfonyl chloride (300 uL, 1.92 mmol). After stirring at room temperature overnight, the reaction mixture was concentrated under reduced pressure and purified using silica gel chromatography eluting with CH$_2$Cl$_2$-3% MeOH in CH$_2$Cl$_2$. The resulting product (137 mg, 0.33 mmol) was dissolved in EtOH (3 mL) and Pd/C (93 mg, 0.087 mmol) was added. A hydrogen balloon was placed over the reaction mixture for 5.5 hours before it was filtered through celite and concentrated to give (3R)-3-(aminomethyl)-4-[(3,4-dichlorophenyl)sulfonyl]-3,4-dihydroquinoxalin-2(1H)-one, which was used without further purification. LCMS (ES) 385.9.

To a solution of the above product (0.35 mg, 0.091 mmol) in CH$_2$Cl$_2$ (0.9 mL) was added EDCI (55 mg, 0.29 mmol) and HOBt (43 mg, 0.32 mmol). After 1.5 hours, 4-(4,5-dihydro-1H-imidazol-2-yl)benzeneacetic acid (190 mg, 0.93 mmol) was added and the reaction mixture stirred at room temperature overnight. The reaction mixture was diluted with EtOAc (100 mL) and washed with saturated NaHCO$_3$ (1×30 mL) and brine (1×30 mL). After drying over sodium sulfate, filtering and concentrating, the crude material was purified on a 1 mm preparative TLC plate eluting with 5% MeOH in CH$_2$Cl$_2$ to give the title compound. LCMS (ES) 571.9.

EXAMPLE 3

(3R)-4-[(3,4-dichlorophenyl)sulfonyl]-3-[2-({3-[4-(4,5-dihydro-1H-imidazol-2-yl)phenyl]propyl}sulfonyl)ethyl]-3,4-dihydroquinoxalin-2(1H)-one

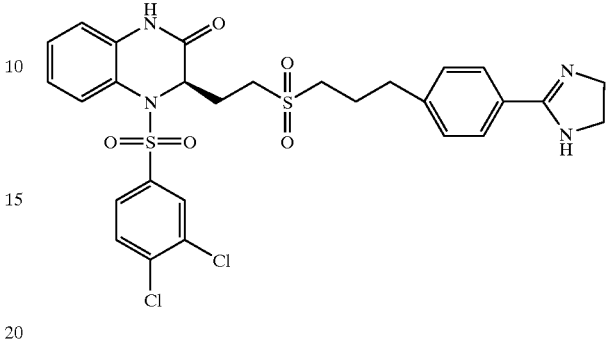

To a solution of methyl {(2R)-1-[(3,4-dichlorophenyl)sulfonyl]-3oxo-1,2,3,4-tetrahydroquinoxalin-2-yl}acetate (Example 1, Step 3, 371 mg, 0.86 mmol) in THF (2 mL) was added LiAlH(tBuO)$_3$ (3 mL, 3 mmol). The reaction mixture was stirred at room temperature for approximately two weeks and was then poured into 1N HCl (30 mL) and extracted with EtOAc (3×20 mL). The combined organics were washed with brine (1×20 mL), dried over sodium sulfate, filtered, and concentrated in vacuo. The crude material was subjected to silica gel chromatography eluting with 2%–7% MeOH in CH$_2$Cl$_2$ to give (3R)-4-[(3,4-dichlorophenyl)sulfonyl]-3-(2-hydroxyethyl)-3,4-dihydroquinoxalin-2(1H)-one (211 mg, 61%). LCMS (ES) 400.8.

To a solution of of the above product (211 mg, 0.53 mmol) in CH$_2$Cl$_2$ (4 mL), Et$_3$N (0.30 mL, 2.10 mmol) and mesyl chloride (0.13 mL, 1.58 mmol) were added. After overnight stirring, the reaction mixture was poured into water and extracted with EtOAc (3×30 mL). Combined organics were washed with brine (1×30 mL), dried over sodium sulfate, filtered and concentrated. Crude material was subjected to silica gel chromatography eluting with 1%-5% MeOH CH$_2$Cl$_2$ to give 219 mg (87% yield) of 2-{(2R)-1-[(3,4-dichlorophenyl)sulfonyl]-3-oxo-1,2,3,4-tetrahydrquinoxalin-2-yl}ethyl methanesulfonate. To a solution of the sulfonate (219 mg, 0.46 mmol) in acetone (4 mL), AcSK (157 mg, 1.37 mmol) was added. After approximately 40 minutes, the reaction mixture was heated to reflux for 30 minutes. After cooling, the crude reaction mixture was diluted with EtOAc (100 mL), washed with water (1×30 ml), washed with brine (1×30 mL), dried over sodium sulfate, filtered, and concentrated to give 87 mg (42% yield) of S-(2-{(2R)-1-[(3,4-dichlorophenyl)sulfonyl]-3-oxo-1,2,3,4-tetrahydroquinoxalin-2-yl }ethyl) ethanethioate, which was used without further purification. LCMS (ES) 458.8.

To a solution of the above product (100 mg, 0.22 mmol) in MeOH (1.5 mL) was added one drop of concentrated HCl. The reaction mixture was heated to reflux, and after overnight refluxing, it was cooled to room temperature and 4-(3-iodopropyl)benzonitrile (118 mg, 0.44 mmol) and Et$_3$N (0.20 mL, 1.46 mmol) were added. After stirring at room temperature for 4.5 hours, the crude reaction mixture was poured into EtOAc (50 mL) and washed with water (1×20 mL) and brine (1×20 mL). The organic layer was then dried over sodium sulfate, filtered, and concentrated in vacuo. Flash chromatography on silica gel eluting with 3%-9% ether in CH₂Cl₂ gave 4 {3-[(2-1(2R)-{(1-[(3,4-dichlorophenyl)sulfonyl]-3-oxo-1,2,3,4-tetrahydroquinoxalin-2-yl}ethyl)thio]propyl benzonitrile (57 mg, 47%). LCMS (ES) 559.8.

To a solution of the above product (57 mg, 0.10 mmol) in CH₂Cl₂ (1 mL) at room temperature, was added mCPBA (53 mg, 0.31 mmol). After stirring for 30 minutes the reaction mixture was poured into EtOAc (30 mL) and washed with saturated NaHCO₃ (1×20 mL) and brine (1×20 mL). After drying over sodium sulfate, filtering and concentrating, the crude product was subjected to silica gel chromatography eluting with 5%–20% ether in CH₂Cl₂ to give 48 mg (80%) of 4-{3-[(2-{(2R)-1-[(3,4-dichlorophenyl)sulfonyl]-3-oxo-1,2,3,4-tetrahydroquinoxalin-2-ylethyl)sulfonyl] propyl}benzonitrile. HCl$_{(g)}$ was bubbled into a solution of this di-sulfonyl benzonitrile (0.40 mg, 0.68 mmol) in EtOH (2 mL) cooled to 0° C. for approximately 2 minutes until saturation was reached. The reaction was capped and allowed to warm to room temperature. After overnight stirring, the reaction mixture was concentrated in vacuo, re-dissolved in EtOH (2 mL), and ethylene diamine (0.01 mL, 0.12 mmol) was added After two hours, the crude reaction mixture was concentrated and purified directly on a preparative TLC plate eluting with 10% MeOH, 1% NH₄OH in CHCl₃ giving 28 mg of the title compound (43% overall yield for three steps). ¹HNMR (400 MHz, CDCl₃) δ 7.70 (d, J=8.05 Hz, 2H), 7.68–7.70 (m, 1H), 7.42–7.45 (m, 1H), 7.43 (d, J=595 Hz, 1H), 7.21–7.29 (m, 2H), 7.18 (d, J=8.05 Hz, 3H), 6.77 (d, J=6.94 Hz, 1H), 4.67 (dd, J=10.06, 5.40 Hz, 1H), 3.78 (s, 4H), 3.04–3.20 (bm, 2H), 2.89 (t, J=7.81 Hz, 2H), 2.78 (t, J=7.17 Hz, 2H), 2.05–2.17 (m, 3H), 1.80–1.90 (m, 1H).

EXAMPLE 4

(3R)-4-[(3,4-dichlorophenyl)sulfonyl]-3-{5-[4-(4,5-dihydro-1H-imidazol-2-yl)-phenyl]pentyl}-3,4-dihydroquinoxalin-2(1H)-one

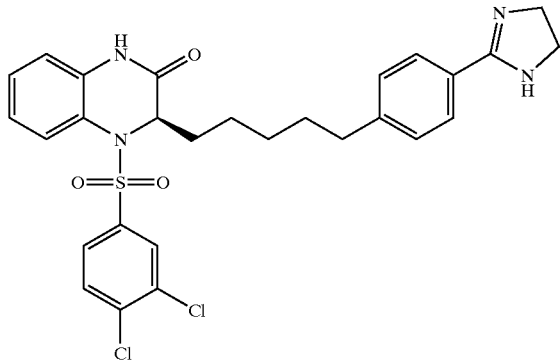

To a solution of 2-fluronitrobenzene (3.70 g, 26.06 mmol) and (2R)-2-aminopent-4-enoic acid (3.00 g, 26.06 mmol) in MeOH (30 mL), was added NaHCO₃ (4.82 g, 57.33 mmol), and the reaction mixture was refluxed overnight. After cooling, concentrating, and chasing with benzene (3×30 mL), the crude product was dried on high vacuum pump overnight to give (2R)-2-[(2-nitrophenyl) amino]-pent-4-enoic acid, which was then dissolved in MeOH, cooled to 0° C. and saturated with HCl$_{(g)}$. The reaction was capped and the reaction mixture was stirred at room temperature overnight, concentrated, and then subjected to silica gel chromatography eluting with 40%–60% CH₂Cl₂ in hexanes to give methyl (2R)-2-[(2-nitrophenyl) amino]pent-4-enoate (3.75 g, 57% overall yield for 2 steps). Methyl (2R)-2-[(2-nitrophenyl)amino]pent-4-enoate was dissolved in MeOH (70 mL) and SnCl₂.H₂O (16.84 g, 74.63 mmol) was added After refluxing overnight, the reaction mixture was cooled and concentrated under reduced pressure. The crude material was poured into EtOAc and saturated NaHCO₃ and extracted with EtOAc (3×100 mL). The combined organics were then washed with NaHCO₃ (1×50 mL) and brine (1×50 mL), dried over sodium sulfate and concentrated in vacuo. The crude product was purified by flash chromatography on silica gel, eluting with 25%–40% EtoAc in Hexanes to give 1.31 g (47%) of (3R)-3-allyl-3,4-dihydroquinoxalin-2(1H)-one. LCMS (ES) m/z 189.3 (M+H)⁺.

To a solution of the above product (506 mg, 2.69 mmol) in pyridine (10 mL) was added 3,4-dichlorobenzenesulfonyl chloride (0.84 mL, 5.38 mmol). After stirring at room temperature overnight, the reaction mixture was concentrated under reduced pressure and purified using silica gel chromatography eluting with 1%–5% ether in CH₂Cl₂ to give 752 mg (70%) of (3R)-3-allyl-4-[3,4-dichlorophenyl) sulfonyl]-3,4-dihydroquinoxalin-2(1H)-one. LCMS (ES) 526.3.

To a solution of the above product (144 mg, 0.36 mmol) in CH₂Cl₂ (7 mL), 4-but-3-enylbenzonitrile (57 mg, 0.36 mmol) and Grubb's catalyst (30 mg, 0.04 mmol) were added and the resulting mixture heated to reflux. After the reaction mixture had refluxed for five days, an additional 30 mg of Grubb's catalyst were added. After refluxing for an additional five hours, the reaction mixture was cooled and purified directly by flash chromatography on silica gel eluting with 2%–10% ether in CH₂Cl₂ to give 36 mg (19%) of 4-((3E)-5-{(2R)-1-[(3,4-dichlorophenyl)sulfonyl]-3-oxo-1,2,3,4-tetrahydroquinoxalin-2-yl}pent-3-enyl)benzonitrile. LCMS (ES) 526.3.

The above product was used to provide (3R)-4-[(3,4-dichlorophenyl)sulfonyl]-3-{(2E)-5-[4-(4,5-dihydro-1H-imidazol-2-yl)phenyl]pent-2-enyl}-3,4-dihydroquinoxalin-2(1H)-one via the methods previously described in Example 1, and the resulting crude product (39 mg, 0.07 mmol) was dissolved in EtOAc (4 mL). Pd/C (45 mg, 4.22 mmol) was added to the solution and a hydrogen balloon was placed over the reaction mixture. After overnight stirring, the reaction mixture was filtered through a pad of celite and concentrated under reduced pressure. The crude product was purified by flash chromatography on silica gel eluting with 10% MeOH in CH₂Cl₂ to 10% MeOH in CH₂Cl₂ with 1% NH₄OH to give title compound (12 mg, 31%). LCMS (ES) 571.3.

EXAMPLE 5

4-(5,6,7,8-tetrahydro-1,8-naphthyridin-2-yl)butyl}
(2R)-1-[(3,4-dichlorophenyl)-sulfonyl]-3-oxo 1,2,3,
4-tetrahydroquinoxalin-2-yl}acetate

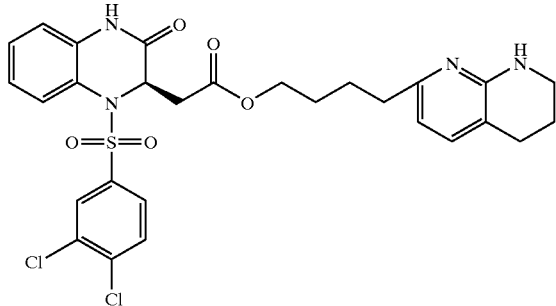

To a solution of {(2R)-1-[(3,4-dichlorophenyl)sulfonyl]-3-1,2,3,4-tetrahydroquinoxalin-2-yl}acetic acid (Example 1, Step 4, 72 mg, 0.17 mmol) in CH$_2$Cl$_2$ (2 mL), Et$_3$N (0.05 mL, 0.35 mmol), EDCI (50 mg, 0.26 mmol), and HOBt (35 mg, 0.26 mmol) and 5,6,7,8-tetrahydro-1,8-naphthyridine-2-butanol (71 mg) were added. The reaction mixture was stirred at room temperature for three days. The crude reaction mixture was purified directly by flash chromatography on silica gel eluting with 5%–10% MeOH in CHCl$_3$, and then re-purified on preparative TLC plates eluting with 60% Acetone in CHCl$_3$ to give 35 mg (33%) of the title compound. LCMS (ES) 602.8.

EXAMPLE 6

N-(2-{(2R)-1-[(3,4-dichlorophenyl)sulfonyl]-3-oxo-1,2,3,4-tetrahydroquinoxalin-2-yl}ethyl)-2-[4-(4,5-dihydro-1H-imidazol-2-yl)phenyl]acetamide

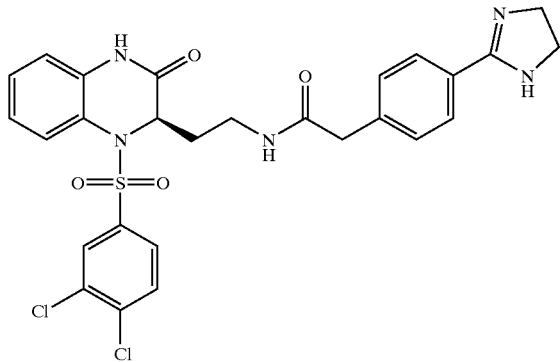

To a solution of methyl [(2R)-3-oxo-1,2,3,4-tetratydroquinoxalin-2-yl]acetate (Example 1, Step 2, 3.3 g, 15 mmol) in THF (15 mL) at 0° C., was added LiAlH (tBuO)$_3$ (45 mL, 45 mmol 1 M in THF). The reaction mixture was allowed to warm to room temperature and stirred overnight. An additional 20 mL of LiAlH(tBuO)$_3$ were added. After overnight stirring, the crude reaction mixture was poured into diluted HCl (pH~2) and extracted with EtOAc (3×50 mL). The water layer was filtered and then extracted again with EtOAc (3×50 mL). Combined organics were dried over sodium sulfate, filtered, and concentrated in vacuo, and the crude product was subjected to silica gel chromatography, eluting with 2%–7% MeOH in CH$_2$Cl$_2$ to give 600 mg (21%) of (3R)-3-(2-hydroxyethyl)-3,4-dihydroquinoxalin-2(1H)-one. LCMS (ES): m/z 193.1 (M+H)$^+$.

To a solution of the above product (514 mg, 2.68 mmol) in CH$_2$Cl$_2$ (10 mL) at 0° C, MsCl (0.45 mL, 5.81 mmol) and Et$_3$N (1.25 mL, 8.96 mmol) were added. The reaction mixture was allowed to warm to room temperature. After overnight stirring, the crude reaction mixture was poured into water and extracted with EtOAc (3×20 mL). The combined organics were washed with water (1×20 mL) and brine (1×20 mL), dried over sodium sulfate, filtered, and concentrated. This crude residue was taken up in DMF (5 mL) and NaN$_3$ (509 mg, 7.83 mmol) was added. The reaction mixture was heated to 80° C., and after two hours the reaction mixture was cooled, diluted with EtOAc and washed with water (2×50 mL) and brine (1×50 mL). The organic layer was dried over sodium sulfate, filtered, and concentrated to give (3R)-3-(2-azidoethyl)-3,4-dihydroquinoxalin-2(1H)-one, which was used without further purification.

To a solution of the above product (427 mg, 1.97 mmol) in pyridine (3 mL) was added 3,4-dichlorobenzenesulfonyl chloride (1 mL, 6.40 mmol). After stirring at room temperature overnight, the reaction mixture was concentrated under reduced pressure and purified using silica gel chromatography eluting with pure CH$_2$Cl$_2$–2% MeOH in CH$_2$Cl$_2$. The resulting azide (156 mg, 2.37 mmol) was dissolved in EtOH (3 mL) and Pd/C (cat.) was added. A hydrogen balloon was placed over the reaction. After overnight stirring, the crude reaction mixture was filtered through celite and concentrated to (3R)-3-(2-aminoethyl)-4-[(3,4-dichlorophenyl)sulfonyl]-3,4-dihydroquinoxalin-2(1H)-one, which was used without further purification.

To a solution of the above product (0.30 mg, 0.08 mmol) in CH$_2$Cl$_2$ (0.5 mL), Et$_3$N (0.03 mL, 0.23 mmol), 4-(4,5-dihydro-1H-imidazol-2-yl)benzene-acetic acid (31 mg, 0.15 mmol), EDCI (29 mg, 0.15 mmol) and HOBt (20 mg, 0.15 mmol) were added. After overnight stirring, the crude reaction mixture was purified directly on a preparative TLC plate eluting with 5% MeOH in CH$_2$Cl$_2$ (2×) to give the title compound. LCMS (ES) 585.7.

EXAMPLE 7

2-[(2R)-1-(3,4-difluorobenzoyl)-3-oxo-1,2,3,4-tethydroquinoxalin-2-yl]-N-{2-[4-(4,5-dihydro-1H-imidazol-2-yl)phenyl]ethyl}acetamide

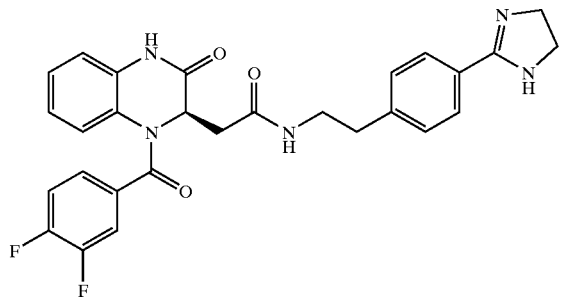

To a solution of methyl [(2R-3-oxo-1,2,3,4-tetrahydroquinoxalin-2-yl]acetate (Example 1, Step 2, 210 mg, 0.95 mmol) in THF (5 mL), was added 4-pyrrolidinopyridine (141 mg, 0.95 mmol) and 3,4-difluorobenzoyl chloride (0.12 mL, 0.95 mmol). After overnight stirring, the crude reaction mixture was poured into 0.5M HCl (50 mL) and extracted (1×50 mL) with EtOAc. The organic layer was then washed with brine, (1×50 mL), dried over sodium sulfate, filtered, and concentrated under reduced pressure. The crude product was subjected to silica gel chromatography eluting with 10%–15% Ether in $CH_2Cl_2$ to give 304 mg (88%) of methyl [(2R)-1-3,4-difluorobenzoyl)-3-oxo-1,2,3,4-tetrahydroquinoxalin-2-yl]-acetate. LCMS (ES) 361.2 m/z $(M+H)^+$.

To a solution of the above product (304 mg, 0.84 mmol) in MeOH (4 mL), 1M NaOH (0.93 mL, 0.93 mmol) was added. After stirring at room temperature for five hours, the reaction mixture was brought to a pH of 7 with 1M HCl. The resulting solution was concentrated in vacuo, chased with toluene (2×20 mL), and placed on the high vacuum pump to give [(2R)-1-(3,4-difluorobenzoyl)-3-oxo-1,2,3,4-tetrahydroquinoxalin-2-yl]acetic acid, which was used without further purification. LCMS (ES) 347.2 m/z $(M+H)^+$.

To a solution of the above product (100 mg, 0.29 mmol) in $CH_2Cl_2$ (3 mL), $Et_3N$ (0.10 mL, 0.72 mmol), 2-[4-(4,5-dihydro-1H-imidazol-2-yl)phenyl]ethanmine (66 mg, 0.35 mmol), EDCI (111 mg, 0.58 mmol), and HOAt (79 mg, 0.58 mmol) were added. After overnight stirring, the reaction mixture was purified directly by flash chromatography on silica gel eluting with 5%–10% MeOH in $CH_2Cl_2$ with 1% $NH_4OH$, and re-purified by silica gel chromatography eluting with 10% MeOH in $CH_2Cl_2$ with 1% $NH_4OH$ to give 31 mg (21%) of the title compound. LCMS (ES) 518.4 m/z $(M+H)^+$.

EXAMPLE 8

2-[(2R)-1-benzyl-3-oxo-1,2,3,4-tetrahydroquinoxalin-2-yl]-N-{2-[4-(4,5-dihydro-1H-imidazol-2-yl)phenyl]ethyl}acetamide

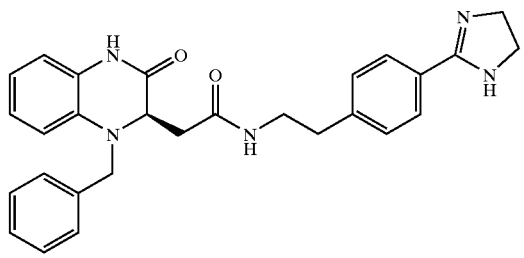

To a solution of methyl [(2R)-3-oxo-1,2,3,4-tetrahydroquinoxalin-2-yl]acetate (Example 1, Step 2, 299 mg, 1.36 mmol) in DMF (5 mL), $Cs_2CO_3$ (885 mg, 2.72 mmol) and then (bromomethyl)benzene (0.48 mL, 4.07 mmol) were added. After overnight stirring, the crude reaction mixture was poured into saturated $NaHCO_3$ (50 mL) and extracted with EtOAc (3×50 mL). The combined organics were then washed with water (2×50 mL) and brine (1×50 mL), dried over sodium sulfate, filtered, and concentrated in vacuo. The crude product was subjected to silica gel chromatography eluting with 15%–25% EtOAc in Hexanes to give 131 mg (31%) methyl [(2R)-1-benzyl-3-oxo-1,2,3,4-tetrahydroquinoxalin-2-yl]acetate. LCMS (ES) 311.3 m/z $(M+H)^+$.

To a solution of the above product (131 mg, 0.42 mmol) in MeOH (5 mL), 1M NaOH (0.63 mL, 0.63 mmol) was added. After stirring at room temperature for five hours, the reaction mixture was brought to a pH of 7 with 1M HCl. The resulting solution was concentrated under reduced pressure, chased with toluene (2×20 mL), and placed on the high vacuum pump to give [(2R)-1-benzyl-3-oxo-1,2,3,4-tetrahydroquinoxalin-2-yl]acetic acid, which was used without further purification. LCMS (ES) 297.3 m/z $(M+H)^+$.

To a solution of the above product (0.90 mg, 0.30 mmol) in $CH_2Cl_2$ (3 mL), $Et_3N$ (0.13 mL, 0.91 mmol), 4-(4,5-dihydro-1H-imidazol-2-yl)benzeneethanamine (69 mg, 0.36 mmol), EDCI (117 mg, 0.61 mmol), and HOAt (83 mg, 0.61 mmol) were added. After overnight stirring, the reaction mixture was purified directly by flash chromatography on silica gel eluting with 10% MeOH in $CH_2Cl_2$ with 1% $NH_4OH$. The title compound was obtained from HPLC purification (1.4 mg, 1%). LCMS (ES) 518.4 m/z $(M+H)^+$.

EXAMPLE 9

2-[(2R)-7-Chloro-1-(2-naphthylsulfonyl)-3-oxo-1,2,3,4-tetrahydroquinoxalin-2-yl]-N-{2-[4-(4,5-dihydro-1H-imidazol-2-yl)phenyl]ethyl}acetamide

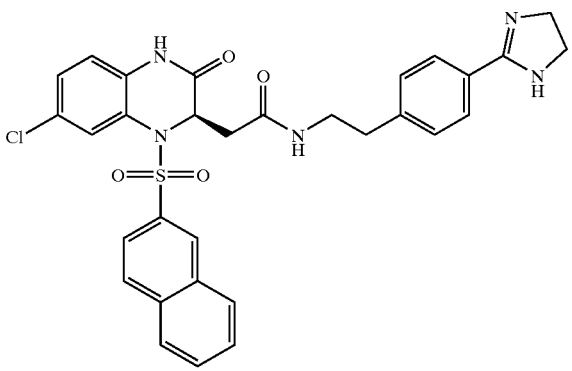

To a solution of dimethyl D-aspartate(2.0 g, 10.12 mmol) in acetone (20 mL) was added $Et_3N$ (2.96 mL, 21.25 mmol) and 4-chloro-2-fluoro-1-nitrobenzne (1.78 g, 10.12 mmol), and the resulting solution was heated to reflux. After refluxing overnight, the reaction mixture was cooled and then concentrated under reduced pressure. The crude residue was taken up in EtOAc (100 mL) and washed with water (1×20 mL) and brine (1×20 mL), dried over sodium sulfate, filtered, and concentrated. The crude product was subjected to silica gel chromatography eluting with 30% hexanes in $CH_2Cl_2$ to pure $CH_2Cl_2$ to give 852 mg (27%) of dimethyl (2R)-2-[(5-chloro-2-nitrophenyl)amino]butanedioate which was then dissolved in MeOH (20 mL) and mixed with $SnCl_2.H_2O$ (1.82 g, 8.07 mmol). After refluxing overnight, the reaction mixture was cooled and concentrated in vacuo. The crude residue was taken up in EtOAc (150 mL) and washed with saturated $NaHCO_3$ (1×50 mL). The aqueous layer was then extracted with EtOAc (2×50 mL), and the combined organics were washed with brine (1×50mL), dried over sodium sulfate, filtered, and concentrated. The crude product was purified by flash chromatography on silica gel eluting with 2%–10% ether in $CH_2Cl_2$ to give 530 mg (77%) of methyl[(2R)-7-chloro-3-oxo-1,2,3,4-tetrahydroquinoxalin-2-yl]acetate. LCMS (ES) 255.5 m/z $(M+H)^+$.

To a solution of the above product (203 mg, 0.80 mmol) in MeOH (7 mL) at room temperature, 1M NaOH (1.00 mL, 1.00 mmol) was added. The reaction was progressing slowly four hours, so it was neutralized with 1M HCl and then re-subjected to the same reaction conditions, except using only 5 mL of MeOH. An additional 0.4 mL of 1M NaOH was added after four hours, and the reaction was complete after an additional three hours of stirring. The crude reaction mixture was concentrated under reduced pressure, then re-dissolved in EtOAc. After neutralizing with 1M HCl, the crude product mixture was concentrated to give the carboxylic acid (255 mg, 0.79 mmol) which was dissolved in $CH_2Cl_2$ and mixed with $Et_3N$ (0.55 ml, 3.95 mmol), EDCI (454 mg, 2.37 mmol), HOBt (320 mg, 2.37 mmol), and 4-(2-aminoethyl)benzonitrile (115 mg, 0.79 mmol). After overnight stirring, the crude reaction mixture was diluted with EtOAc (100 mL) and washed with water (1×30 mL) and brine (1×30 mL). After drying over sodium sulfate, filtering, and concentrating, the crude product was purified by flash chromatography eluting with 1%–5% MeOH in $CH_2Cl_2$ to give 255 mg (88%) of 2-[(2R)-7-chloro-3-oxo-1,2,3,4-tetrahydroquinoxalin-2-yl]-N-[2-(4-cyanophenyl)ethyl]acetamide. LCMS (ES) 369.6 m/z $(M+H)^+$.

To a solution of the above product (200 mg, 0.54 mmol) in pyridine (2.5 mL) was added 2-napthalenesulfonyl chloride (369 mg, 1.63 mmol). After stirring at room temperature for one hour, the reaction mixture was concentrated in vacuo and subjected to silica gel chromatography eluting with 1%–5% MeOH in $CH_2Cl_2$ to give 270 mg (89%) of 2-[(2R)-7-chloro-1-(2-naphthylsulfonyl)-3-oxo-1,2,3,4-tetrahydroquinoxalin-2-yl]-N-[2-(4-cyanophenyl)ethyl]acetamide. LCMS (ES) 559.6 m/z $(M+H)^+$.

Conversion of the above cyano compound into the corresponding phenethyl imidazoline via the methods previously described in Example 1 gave the title compound. LCMS (ES) 602.5.

EXAMPLE 10

2-{(2R)-1-[(3,4-dichlorophenyl)sulfonyl]-4-methyl-3-oxo-1,2,3,4-tetrahydroquinoxalin-2-yl}-N-{2-[4-(4,5-dihydro-1H-imidazol-2-yl)phenyl]ethyl}acetamide

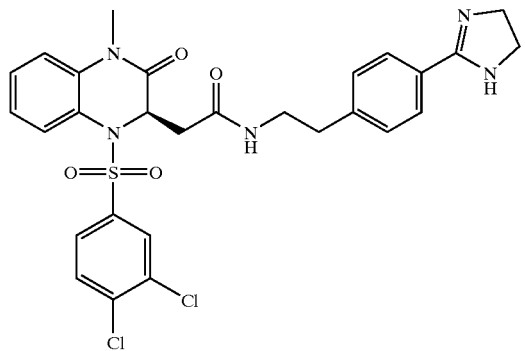

To a solution of methyl [($^2$R)-3-oxo-1,2,3,4-tetrahydroquinoxalin-2-yl]acetate (Example 1, Step 2, 650 mg, 2.95 mmol) in DMF (5 mL) at 0° C. was added NaH (142 mg, 3.54 mmol). After stirring at 0° C. for 20 minutes, MeI (220 uL, 3.54 mmol) was added and the reaction mixture was stirred for an additional 15 minutes at 0° C. The reaction mixture was then diluted with water (10 mL) and extracted with EtOAc (2×50 mL). Combined organics were washed with water (1×50 mL), dried over sodium sulfate, filtered, and concentrated to give methyl [(2R)-4-methyl-3-oxo-1,2,3,4-tetrahydroquinoxalin-2-yl]acetate, which was used without further purification. LCMS (ES) 235.1 m/z $(M+H)^+$.

To solution of above product (300 mg, 1.28 mmol) in pyridine (1.5 ml), 3,4-dichlorosulfonyl chloride (471 mg, 1.92 mmol) was added. After stirring at room temperature for three hours, 50 mL of toluene was added to the reaction mixture and it was concentrated in vacuo. The crude residue was taken up in EtOAc (150 mL) and washed with 0.5M HCl (1×20 mL) and brine (1×20 mL). Drying over sodium sulfate, filtering, and concentrating gave methyl {(2R)-1-[(3,4-dichlorophenyl)-sulfonyl]-4-methyl-3-oxo-1,2,3,4-tetrahydroquinoxalin-2-yl}acetate, which was dissolved in MeOH (10 mL) and 1M NaOH (0.25 mL, 0.25 mmol) was added to the solution. Over the course of five hours, an additional 1.78 mL of NaOH was added. The crude reaction mixture was brought to a pH of 2 with 2M HCl and then the solvents were removed in vacuo and the crude residue was chased with toluene (1×50 mL). The crude residue was taken up in 2% MeOH in $CH_2Cl_2$ and filtered to remove inorganic solids. Concentration of the filter gave crude product which was purified by flash chromatography on silica gel eluting with 2%–20% MeOH in $CH_2Cl_2$ to give 40 mg (7% for 2 steps) of {(2R)-1-[(3,4-dichlorophenyl)sulfonyl]-4-methyl-3-oxo-1,2,3,4-tetrahydroquinoxalin-2-yl}acetic acid. LCMS (ES) 428.8.

To a solution of the above product (40 mg, 0.093 mmol) in $CH_2Cl_2$ cooled to 0° C., oxalyl chloride (5 uL, mmol) and DMF (10 uL) were added. An additional 5 uL of oxalyl chloride were added after thirty minutes, and then another 9 uL of oxalyl chloride was added fifteen minutes later. After a total reaction time of 75 minutes at 0° C., the reaction mixture was concentrated under reduced pressure and then chased with toluene (3×20 mL). Residue was taken up in $CH_2Cl_2$ (1 mL) and added over to a solution of 4-(4,5-dihydro-1H-imidazol-2-yl)benzeneethanamine (19.3 mg 0.102 mmol) in $CH_2Cl_2$ (2 mL). After stirring at room temperature for fifteen minutes, the crude reaction mixture was concentrated, chased with toluene (1×20 mL) and subjected to silica gel chromatography eluting with 5%–20% MeOH in $CHCl_3$ to yield 10 mg (18% for 2 steps) the tide compound. LCMS (ES) 599.9.

EXAMPLE 11

2-[(2R)-1-(2-naphthyl[$^{35}$S]sulfonyl)-3-oxo-1,2,3,4-tetrahydroquinoxalin-2-yl]-N-{2-[4-(4,5-dihydro-1H-imidazol-2-yl)phenyl]ethyl}acetamide

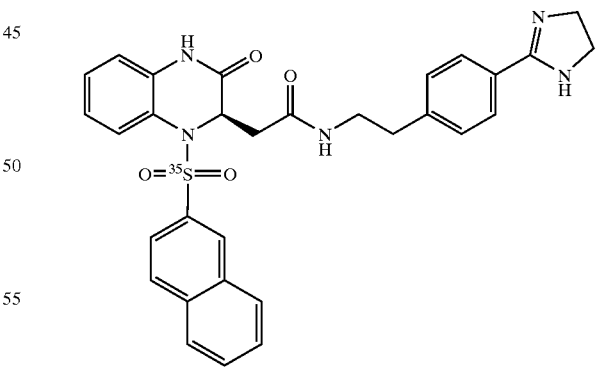

To the ethanolic solution of [$^{35}$S]naphthylenesulfonic acid (85/15 1-isomer/2-isomer) is added 3 mg of sodium bicarbonate. The solution is then concentrated to dryness with a nitrogen stream and dried in vacua for 2 h. Methylene chloride (10 mL), and DMF (2 uL) are added, followed by oxalyl chloride (75 uL). The reaction mixture is aged at room temperature for 18 h with periodic venting to prevent gas buildup. The reaction mixture is quenched with water (3 mL), diluted with 20 mL methylene chloride, and the layers separated. The reaction mixture is then washed with 10% sodium bicarbonate solution (2×5 mL). The organic phase is dried twice over sodium sulfate and filtered to afford [$^{35}$S] naphthylenesulfonyl chloride (stock solution in methylene chloride) in a 90% radiochemical yield.

2-[(2R)-3-Oxo-1,2,3,4-tetrahydroquinoxalin-2-yl]-N-[2-(4-cyanophenyl)ethyl]acetamide (6.5 mg) and di-tert-butylmethyl pyridine (5 mg) were dissolved in 20 uL of pyridine (with heating). The methylene chloride solution of [$^{35}$S]naphthylenesulfonyl chloride ( 350 mCi) was distilled at 65° C. to approximately a volume of 75 uL and added to the amine solution. The mixture is aged overnight at room temperature. The reaction mixture is quenched into ethyl acetate (10 mL), extracted with saturated bicarbonate solution (2×2 mL), brine (1×2 mL), dried over MgSO$_4$, filtered, and concentrated to provide 2-[(2R)-1-(2-naphthyl[$^{35}$S]sulfonyl)-3-oxo-1,2,3,4-tetrahydroquinoxalin-2-yl]-N-[2-(4-cyanophenyl)ethyl]acetamide; radiochemical yield of 2-isomer[$^{35}$S]sulfonamide averages 4–5%.

The crude [$^{35}$S]cyano-sulfonamide is dissolved in ethanol (10 mL) and HCl gas is bubbled through the solution for 5 min. The reaction mixture is aged overnight at room temperature, concentrated to a residue and redissolved in ethanol (5 mL). Ethylene diamine (100 uL) is added and the mixture aged at room temperature for 16 h. The crude reaction mixture is concentrated, dissolved in 20/80 CH$_3$CN/0/1% TFA and loaded onto a Zorbax RX C8 semi-preparative column. Elution with 29/71 CH$_3$CN/0/1% TFA affords radiochemically pure title compound To remove any remaining mass impurities, an additional purification by semi-preparative HPLC (Luna C8, 28/72 CH$_3$CN/0/1% TFA) gave 8.0 mCi of radiochemically and chemically pure title compound.

The procedures described above were followed in the preparation of the compounds listed in the following tables. The starting materials are commercially availabel, known in the literature, or may be prepared according to methods well known in the art.

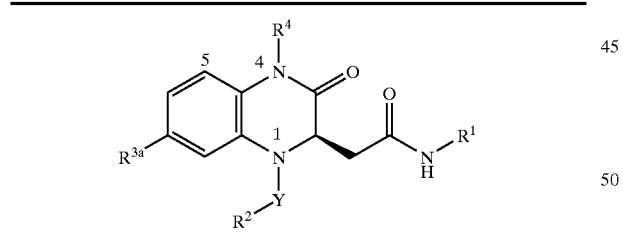

| Ex. | R$^1$ | Y | R$^2$ | R$^{3a}$ | R$^4$ | MS (ES) |
|---|---|---|---|---|---|---|
| 12 | (CH$_2$)$_2$-(4-(4,5-dihydro-1-methyl-2-imidazolyl)-Ph) | SO$_2$ | 2-naphthyl | Cl | H | 616.6 |
| 13 | (CH$_2$)$_2$-(4-(4,5-dihydro-2-imidazolyl)-Ph) | SO$_2$ | 2-naphthyl | H | H | 568.2 |
| 14 | (CH$_2$)$_2$-(4-(4,5-dihydro-2-imidazolyl)-Ph) | SO$_2$ | 3,4-diCl-Ph | F | H | 604.2 |
| 15 | (CH$_2$)$_2$-(4-(2-imidazolyl)-Ph) | SO$_2$ | 2-naphthyl | H | H | 566.6 |
| 16 | (CH$_2$)$_2$-(4-(2-imidazolyl)-Ph) | SO$_2$ | 2-naphthyl | Cl | H | 600.6 |
| 17 | (CH$_2$)$_2$-(4-(4,5-dihydro-2-imidazolyl)-Ph) | SO$_2$ | Ph | Cl | H | 553.6 |
| 18 | (CH$_2$)$_2$-(4-(4,5-dihydro-2-imidazolyl)-Ph) | C(O) | 3,4-diCl-Ph | H | H | 550.2 |

-continued

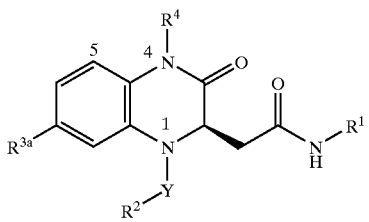

| Ex. | R$^1$ | Y | R$^2$ | R$^{3a}$ | R$^4$ | MS (ES) |
|---|---|---|---|---|---|---|
| 19 | (CH$_2$)$_2$-(4-(1-imidazolyl)-Ph) | SO$_2$ | 3,4-diCl-Ph | H | H | 584.2 |
| 20 | (CH$_2$)$_2$-(4-(1-imidazolyl)-Ph) | SO$_2$ | 2-naphthyl | Cl | H | 600.6 |
| 21 | (CH$_2$)$_2$-(4-(4,5-dihydro-2-imidazolyl)-Ph) | C(O) | 4-Cl-Ph | H | H | 516.3 |
| 22 | (CH$_2$)$_2$-(4-(4,5-dihydro-2-imidazolyl)-Ph) | C(O) | 2-naphthyl | H | H | 566.6 |
| 23 | (CH$_2$)$_2$-(4-(1,2,4-triazol-4-yl)-Ph) | SO$_2$ | 2-naphthyl | Cl | H | 601.6 |
| 24 | (CH$_2$)$_2$-(4-(1,2,4-triazol-4-yl)-Ph) | SO$_2$ | 3,4-diCl-Ph | H | H | 585.3 |
| 25 | 4-(4,5-dihydro-2-imidazoyl)-Ph | SO$_2$ | 3,4-diCl-Ph | H | H | 557.8 |
| 26 | (CH$_2$)$_2$-(4-(1-imidazolyl)-Ph) | SO$_2$ | 5-Cl-2-thienyl | H | H | 556.2 |
| 27 | 4-(1-imidazolyl)-Ph | SO$_2$ | 3,4-diCl-Ph | H | H | 555.8 |
| 28 | (CH$_2$)$_2$-(4-(4,5-dihydro-2-imidazolyl)-Ph) | C(O) | 3-Cl-Ph | H | H | 516.3 |
| 29 | (CH$_2$)$_2$-(4-(4,5-dihydro-2-imidazolyl)-Ph) | CO$_2$ | CH$_2$Ph | H | H | 512.4 |
| 30 | (CH$_2$)$_2$-(4-(4,5-dihydro-2-imidazolyl)-Ph) | C(O) | c-Hex | H | H | 488.4 |
| 31 | (CH$_2$)$_2$-(4-(4,5-dihydro-2-imidazolyl)-Ph) | SO$_2$ | CH$_3$ | Cl | H | 490.5 |
| 32 | (CH$_2$)$_2$-(1,2,4-triazol-3-yl) | SO$_2$ | 3,4-diCl-Ph | H | H | 509.2 |

What is claimed is:
1. A compound of formula I

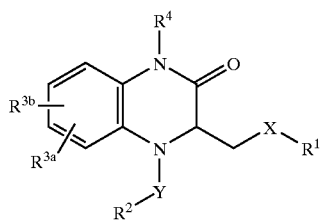

and pharmaceutically acceptable salts thereof, wherein
X is selected from
  (1) —(CH$_2$)$_m$C(O)NR$^b$—,
  (2) —(CH$_2$)$_m$NR$^b$C(O)—,
  (3) —(CH$_2$)$_m$C(O)O—,
  (4) —(CH$_2$)$_m$S(O)$_m$—,
  (5) —(CH$_2$)$_m$O—,
  (6) —(CH$_2$)$_m$NR$^b$—,
  (7) —C(O)—,
  (8) HC=CH, and
  (9) —(CH$_2$)$_m$—;
Y is selected from
  (1) —C(O)—,
  (2) —C(O)O—,
  (3) —SO$_2$— and,
  (4) —CH$_2$—;

R[1] is (CH$_2$)$_n$-phenyl substituted with a group selected from 1-imidazolyl, 2-imidazolyl, 4,5-dihydro-2-imidazolyl, and 1,2,4-triazol-4-yl; wherein the imidazolyl, dihydroimidazolyl, and triazolyl rings are each optionally substituted with 1 or 2 C$_{1-4}$alkyl groups;

R$^2$ is selected from:
  (1) C$_{1-6}$ alkyl optionally substituted with 1 to 3 halogen atoms,
  (2) C$_{3-7}$ cycloalkyl,
  (3) aryl,
  (4) ara-C$_{1-4}$alkyl, wherein aryl and aralkyl are optionally substituted with 1 to 4 groups independently selected from halogen, C$_{1-4}$ alkyl optionally substituted with 1 to 5 halogen atoms, hydroxy, C$_{1-4}$ alkoxy optionally substituted with 1 to 5 halogen atoms, nitro, cyano and NR$^b$R$^c$; and wherein aryl is selected from phenyl, naphthyl, pyridyl, isoquinolinyl, and thienyl;

R$^{3a}$ and R$^{3b}$ are independently selected from
  (1) H,
  (2) halogen,
  (3) C$_{1-6}$ alkyl,
  (4) hydroxy,
  (5) cyano,
  (6) nitro,
  (7) C$_{1-6}$ alkoxy, and
  (8) trifluoromethyl;

R$^4$ is selected from
  (1) H,
  (2) C$_{1-4}$ alkyl, optionally substituted with 1-5 halogen atoms,
  (3) C$_{3-7}$ cycloalkyl,
  (4) (CH$_2$)$_p$CO$_2$R$^d$, and
  (5) (CH$_2$)$_p$CONR$^b$R$^c$;

R$^b$ and R$^c$ are independently selected from
  (1) H, and
  (2) C$_{1-6}$ alkyl, or R$^b$ and R$^c$ together complete a 4- to 7-membered ring optionally containing a ring O or N—R$^d$ group;

R$^d$ is H or C$_{1-4}$ alkyl, m is 0,1 or 2;

n is 0 to 10; and p is 1 or 2.

2. A compound of claim 1 wherein Y is SO$_2$.

3. A compound of claim 1 wherein R$^2$ is phenyl optionally substituted with 1 to 3 groups independently selected from halogen, C$_{1-4}$ alkyl optionally substituted with 1 to 5 halogen atoms, hydroxy, C$_{1-4}$ alkoxy optionally substituted with 1 to 5 halogen atoms, nitro, cyano and NR$^b$R$^c$.

4. A compound of claim 1 wherein R$^2$ is naphthyl.

5. A compound of claim 1 wherein X is —C(O)NH—.

6. A compound of claim 1 wherein R$^1$ is (CH$_2$)$_n$-phenyl substituted with a group selected from 1-imidazolyl, 2-imidazolyl and 4,5-dihydro-2-imidazolyl, wherein the imidazolyl and dihydroimidazolyl rings are each optionally substituted with 1 or 2 C$_{1-4}$alkyl groups.

7. A compound of claim 1 wherein R$^1$ is (CH$_2$)$_n$-phenyl substituted with 4,5-dihydro-2-imidazolyl.

8. A compound of claim 1 having the formula Ia:

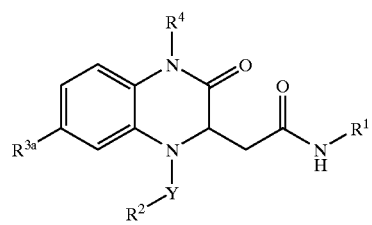

Ia wherein Y is —SO$_2$—, —CO— or CH$_2$; R$^2$ is naphthyl or phenyl optionally substituted with 1 to 3 groups independently selected from halogen, C$_{1-4}$ alkyl optionally substituted with 1 to 5 halogen atoms, hydroxy, C$_{1-4}$ alkoxy optionally substituted with 1 to 5 halogen atoms, nitro, cyano and NR$^b$R$^c$; R$^{3a}$ is hydrogen or a halogen; R$^4$ is hydrogen or C$_{1-4}$alkyl; and R$^1$ is —(CH$_2$)$_{n'}$-(4-substituted phenyl) wherein n' is 0 to 5 and the substituent is selected from 4,5-dihydro-2-imidazolyl optionally substituted with a C$_{1-4}$alkyl group, 2-imidazolyl, 1-imidazolyl, and 1,2,4-triazol-4yl.

9. A compound of claim 8 wherein Y is SO$_2$ or C(O), and R$^2$ is 3,4-dichlorophenyl, 2-naphthyl or 2,4,6-trimethylphenyl.

10. A compound of claim 8 wherein R$^1$ is —(CH$_2$)$_{0-2}$-(4-substituted phenyl) wherein the substituent is selected from 4,5-dihydro-2-imidazolyl optionally substituted with a C$_{1-4}$alkyl group, 2-imidazolyl, 1-imidazolyl and 1,2,4-triazol-4-yl.

11. A compound of claim 1 wherein R$^1$ is —(CH$_2$)$_{0-2}$-(4-substituted phenyl) wherein the substituent is 4,5-dihydro-2-imidazolyl optionally substituted with a C$_{1-4}$alkyl group.

12. A compound of claim 1 wherein the stereoconfiguration at position 3 of the 2-quinoxalinone ring is R.

13. A compound of claim 1 wherein X is selected from C(O)O, CH$_2$, CH$_2$SO$_2$, NHC(O) and CH$_2$NHC(O); Y is —SO$_2$—, —CO— or CH$_2$; R$^2$ is naphthyl or phenyl optionally substituted 1 to 3 groups independently selected from halogen, C$_{1-4}$ alkyl optionally substituted with 1 to 5 halogen atoms, hydroxy, C$_{1-4}$ alkoxy optionally substituted with 1 to 5 halogen atoms, nitro, cyano and NR$^b$R$^c$; R$^{3a}$ is hydrogen or a halogen; R$^4$ is hydrogen or C$_{1-4}$alkyl; and R$^1$ is —(CH$_2$)$_{n'}$-(4-substituted phenyl) wherein n' is 0 to 5 and the substituent is selected from 4,5-dihydro-2-imidazolyl optionally substituted with a C$_{1-4}$alkyl group, 2-imidazolyl, 1-imidazolyl and 1,2,4-tiazol-4-yl.

14. A pharmaceutical composition comprising a therapeutically effective amount of a compound of claim 1 and pharmaceutically acceptable excipients.

15. A method of treatment of osteoarthritis, repetitive motion pain, dental pain, cancer pain, myofascial pain, muscular injury pain, fibromyalgia pain, perioperative pain comprising a step of administering, to a subject in need of such treatment, an effective amount of a compound according to claim 1 or a pharmaceutically acceptable salt thereof.

16. A method of treatment of inflammatory pain caused by chronic obstructive pulmonary disease, asthma, inflammatory bowel disease, rhinitis, pancreatitis, cystitis, uveitis, inflammatory skin disorders, rheumatoid arthritis, edema resulting from trauma associated with burns, sprains or fracture, postsurgical intervention, osteoarthritis, rheumatic disease, teno-synovitis, or gout comprising a step of administering, to a subject in need of such treatment or prevention, an effective amount of a compound according to claim 1 or a pharmaceutically acceptable salt thereof.

17. A method of treatment of pain associated with angina, menstruation or cancer comprising a step of administering, to a subject in need of such treatment or prevention, an effective amount of a compound according to claim 1 or a pharmaceutically acceptable salt thereof.

18. A method of treatment of diabetic vasculopathy, post capillary resistance, insulitis, psoriasis, eczema, spasms of the gastrointestinal tract or uterus, Crohn's disease, ulcerative colitis, or pancreatitis comprising a step of administering, to a subject in need of such treatment, an effective amount of a compound according to claim 1 or a pharmaceutically acceptable salt thereof.

19. A method of treatment of pain caused by pneumoconiosis, including aluminosis, anthracosis, asbestosis, chalicosis, ptilosis, siderosis, silicosis, tabacosis, byssinosis, adult respiratory distress syndrome, bronchitis, allergic rhinitis, vasomotor rhinitis, liver disease, multiple sclerosis, atherosclerosis, Alzheimer's disease, septic shock, cerebral edema, headache, migraine, closed head trauma, irritable bowel syndrome, or nephritis comprising a step of administering, to a subject in need of such treatment or prevention of pain, an effective amount of a compound according to claim 1 or a pharmaceutically acceptable salt thereof.

* * * * *